US012575800B2

(12) United States Patent
Oikawa et al.

(10) Patent No.: US 12,575,800 B2
(45) Date of Patent: Mar. 17, 2026

(54) X-RAY DIAGNOSTIC APPARATUS, CONTROL METHOD FOR X-RAY DIAGNOSTIC APPARATUS, AND X-RAY DIAGNOSTIC SYSTEM

(71) Applicant: CANON MEDICAL SYSTEMS CORPORATION, Otawara (JP)

(72) Inventors: Hirona Oikawa, Nasushiobara (JP); Satoshi Yamashita, Utsunomiya (JP); Mitsunobu Sugeno, Utsunomiya (JP); Satoshi Tanaka, Nasushiobara (JP); Mitsuru Sakata, Yaita (JP); Katsuaki Shinoda, Shioyagun (JP); Takayuki Ishikawa, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 114 days.

(21) Appl. No.: 18/527,454

(22) Filed: Dec. 4, 2023

(65) Prior Publication Data

US 2024/0180504 A1 Jun. 6, 2024

(30) Foreign Application Priority Data

Dec. 5, 2022 (JP) ................................ 2022-194287

(51) Int. Cl.
*A61B 6/00* (2024.01)
*A61B 6/12* (2006.01)
(52) U.S. Cl.
CPC .............. *A61B 6/4405* (2013.01); *A61B 6/12* (2013.01); *A61B 6/4476* (2013.01); *A61B 6/547* (2013.01)

(58) Field of Classification Search
CPC ....... A61B 6/4405; A61B 6/12; A61B 6/4476; A61B 6/547; A61B 6/102; A61B 6/4441; A61B 6/54
See application file for complete search history.

(56) References Cited

U.S. PATENT DOCUMENTS

| | | | |
|---|---|---|---|
| 10,692,240 B2 | 6/2020 | Mostafavi | |
| 2009/0015669 A1* | 1/2009 | Klingenbeck-Regn | ...................... A61B 6/547 348/142 |
| 2016/0181053 A1* | 6/2016 | Wang | ................... A61B 6/4007 378/197 |

FOREIGN PATENT DOCUMENTS

JP 2016-528952 A 9/2016

* cited by examiner

*Primary Examiner* — Kiho Kim
(74) *Attorney, Agent, or Firm* — Oblon, McClelland, Maier & Neustadt, L.L.P.

(57) ABSTRACT

An X-ray diagnostic apparatus of an embodiment includes processing circuitry. The processing circuitry acquires an image of a movable range of a movable unit that can move freely in an examination room where X-ray imaging of a subject is performed, from a camera provided in the examination room, determines the classification of an object present in the movable range on the basis of the image, and controls the operation of X-ray imaging on the basis of the determination results.

20 Claims, 16 Drawing Sheets

| OPTICAL SENSOR | TEMPERATURE | CONTROL |
|:---:|:---:|:---:|
| ○ | ○ | STOP |
| ○ | - | ALERT |
| - | ○ | REDUCE SPEED |
| - | - | NONE |

○ DETECTED / - NOT DETECTED

T 15, 16

⌐102b

| OPTICAL SENSOR | TEMPERATURE | SHAPE | CONTROL |
|---|---|---|---|
| - | ○ | ○ | REDUCE SPEED |
| ○ | ○ | ○ | STOP |
| - | ○ | SMALL IN SIZE | ALERT |
| - | ○ | ELONGATED | REDUCE SPEED |
| ○ | ○ | ELONGATED | REDUCE SPEED |

○ DETECTED / - NOT DETECTED

| OPTICAL SENSOR | TEMPERATURE | SHAPE | LOCATION | CONTROL |
|---|---|---|---|---|
| ○ | ○ | ○ | IN VICINITY OF OPTICAL SENSOR | STOP |
| - | ○ | ○ | NEAR | STOP |
| - | ○ | ○ | ROTATIONAL RANGE | REDUCE SPEED |
| - | ○ | ○ | FAR | ALERT |
| - | ○ | SMALL IN SIZE | IN VICINITY OF OPTICAL SENSOR | ALERT AND REDUCE SPEED |
| ○ | ○ | ELONGATED | IN VICINITY OF OPTICAL SENSOR | REDUCE SPEED |
| ○ | - | - | - | ALERT |

○ DETECTED / - NOT DETECTED

X-RAY DIAGNOSTIC APPARATUS, CONTROL METHOD FOR X-RAY DIAGNOSTIC APPARATUS, AND X-RAY DIAGNOSTIC SYSTEM

CROSS-REFERENCE TO RELATED APPLICATIONS

This application is based upon and claims the benefit of priority from Japanese Patent Application No. 2022-194287, filed on Dec. 5, 2022, the entire contents of which are incorporated herein by reference.

FIELD

Embodiments described herein relate generally to an X-ray diagnostic apparatus, a control method for the X-ray diagnostic apparatus, and an X-ray diagnostic system.

BACKGROUND

Conventionally, for example, an X-ray diagnostic apparatus that can change the location of an X-ray detector by operating an arm such as an X-ray Angiography apparatus has been known. In such an X-ray diagnostic apparatus, when the arm is rotated or moved in a situation where a person is around, the arm may come into contact with the person or the person's leg may be caught by the arm. In some cases, an operator's leg may accidentally be caught on the arm.

BRIEF DESCRIPTION OF THE DRAWINGS

FIG. 6 is a diagram illustrating an example of a decision table according to the first embodiment;

FIG. 15 is a diagram for explaining an example of a positional relation between a C-arm and a person present in an examination room according to the third embodiment;

FIG. 16 is a diagram illustrating an example of a decision table according to the third embodiment.

DETAILED DESCRIPTION

An X-ray diagnostic apparatus of an embodiment includes processing circuitry. The processing circuitry acquires an image of a movable range of a movable unit that can move freely in an examination room where X-ray imaging of a subject is performed, from a camera provided in the examination room, determines the classification of an object present in the movable range on the basis of the image, and controls the operation of X-ray imaging on the basis of the determination results.

Hereinafter, embodiments of an X-ray diagnostic apparatus, a control method for the X-ray diagnostic apparatus, and an X-ray diagnostic system will be described in detail with reference to the accompanying drawings.

First Embodiment

Figure 1:
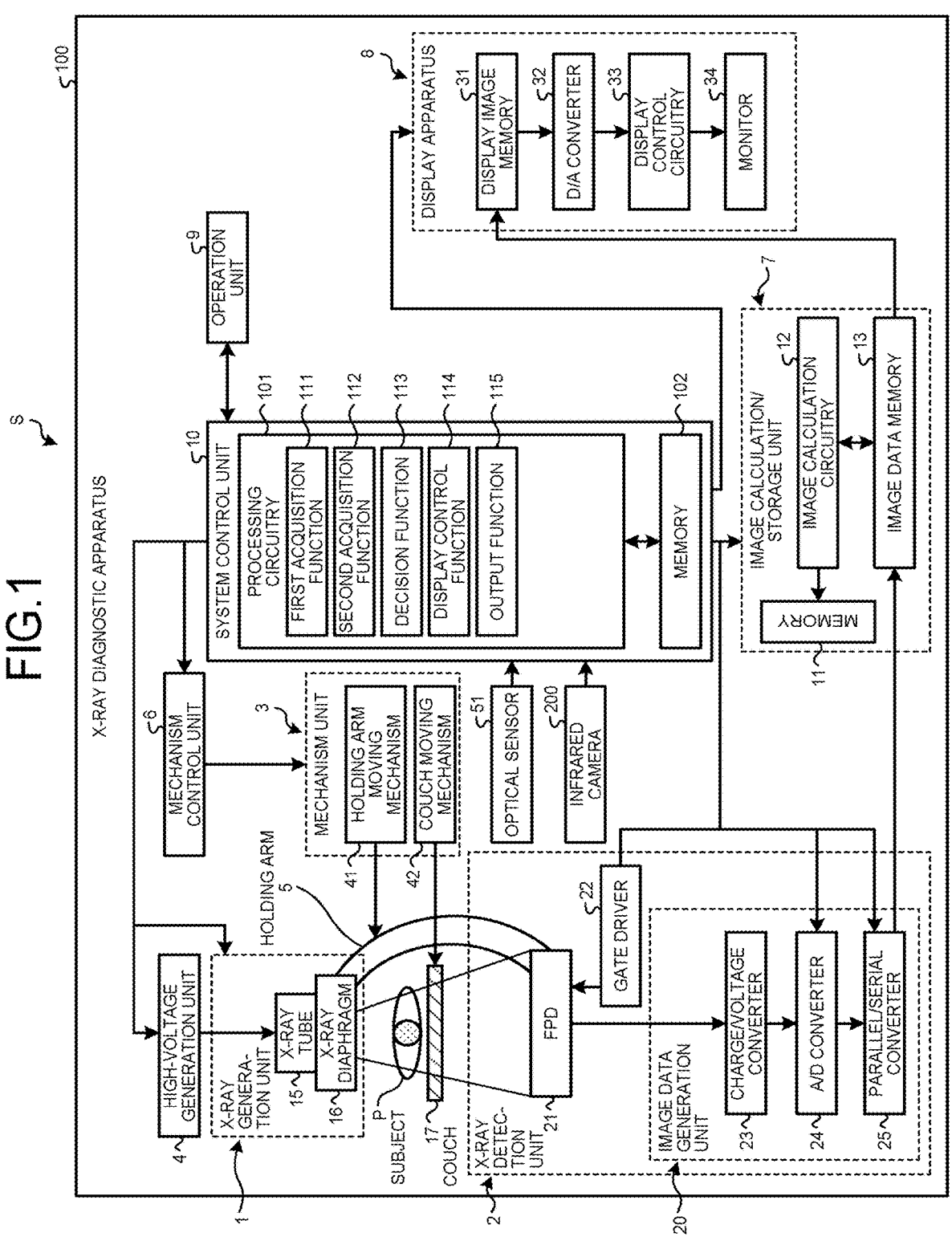
FIG. 1 is a block diagram illustrating an example of a configuration of an X-ray diagnostic apparatus according to a first embodiment.

FIG. 1 is a block diagram illustrating an example of a configuration of an X-ray diagnostic system S according to a first embodiment. The X-ray diagnostic system S includes an X-ray diagnostic apparatus 100 and an infrared camera 200. In FIG. 1, one infrared camera 200 is illustrated. However, the X-ray diagnostic system S may include a plurality of the infrared cameras 200.

First, the X-ray diagnostic apparatus 100 will be described. The X-ray diagnostic apparatus 100 generates X-ray image data capturing an image of a subject P, by irradiating the subject P with X-rays. The subject P is not included in the X-ray diagnostic apparatus 100. For example, the X-ray diagnostic apparatus 100 is used for examination and treatment of cardiovascular system, gastrointestinal tract, urinary tract, orthopedics, interventional radiology (IVR), and the like. However, the usage of the X-ray diagnostic apparatus 100 is not limited to the above.

As illustrated in FIG. 1, the X-ray diagnostic apparatus 100 includes an X-ray generation unit 1, an X-ray detection unit 2, a mechanism unit 3, a high-voltage generation unit 4, a holding arm 5, a mechanism control unit 6, an image calculation/storage unit 7, a display apparatus 8, an operation unit 9, a system control unit 10, a couch 17, and an optical sensor 51.

Moreover, the X-ray generation unit 1 includes an X-ray tube 15 and an X-ray diaphragm 16.

The X-ray tube 15 generates X-rays using high voltage supplied from the high-voltage generation unit 4.

The X-ray diaphragm 16 narrows the X-ray generated by the X-ray tube 15 such that a region of interest of the subject P is selectively irradiated with the X-ray.

The high-voltage generation unit 4 is a high-voltage power supply that generates high voltage under the control of the system control unit 10, and that supplies the generated high-voltage to the X-ray tube 15.

The holding arm 5 holds the X-ray generation unit 1 and the X-ray detection unit 2. The holding arm 5 supports the X-ray generation unit 1 and the X-ray detection unit 2 respectively at both ends, and is also referred to as a C-arm because the shape of which is similar to the letter C in the alphabet. In FIG. 1, the X-ray diagnostic apparatus 100 includes one holding arm 5. However, the X-ray diagnostic apparatus 100 may have a biplane configuration with an additional Ω-arm.

The user mainly performs imaging of the subject P by manually operating the holding arm 5. However, the holding arm 5 may also be automatically operated to capture an image of the subject P according to a predetermined procedure (for example, a routine work procedure and the like).

The holding arm 5 is an example of a movable unit. Moreover, the holding arm 5 is also an example of an imaging unit, because the holding arm 5 holds the X-ray generation unit 1 and the X-ray detection unit 2 that perform X-ray imaging of the subject.

Under the control of the system control unit 10, the mechanism control unit 6 controls a holding arm moving mechanism 41 and a couch moving mechanism 42 so that the rotation and movement of the holding arm 5 and the movement of the couch 17 are adjusted.

The mechanism unit 3 includes the holding arm moving mechanism 41 and the couch moving mechanism 42.

The holding arm moving mechanism 41 is a mechanism for rotating or moving the holding arm 5, and includes a motor, an actuator, and the like, which are not illustrated.

The couch moving mechanism 42 is a mechanism for moving the couch 17, and includes a motor, an actuator, and the like which are not illustrated.

The subject P is placed on the couch 17. While the subject P is placed on the couch 17, the couch 17 can be moved in the vertical direction, the longitudinal direction, and the inclined direction, by the couch moving mechanism 42. The couch 17 is an example of a movable unit.

The couch 17 may be operated by a user or may be automatically operated under the control of processing circuitry 101, which will be described below, according to the positional relation between the holding arm 5 and the subject P, and the like.

The optical sensor 51 is a sensor for detecting the presence of a person around the holding arm 5. For example, the optical sensor 51 is a sensor including a light emitting unit and a light receiving unit, and that detects the presence of a person when the light (for example, laser light and the like) emitted from the light emitting unit and received by the light receiving unit is blocked. There may be a plurality of the optical sensors 51. Moreover, a capacitive proximity sensor or the like may be used instead of the optical sensor. The optical sensor 51 sends the sensing results to the system control unit 10.

Figure 2:
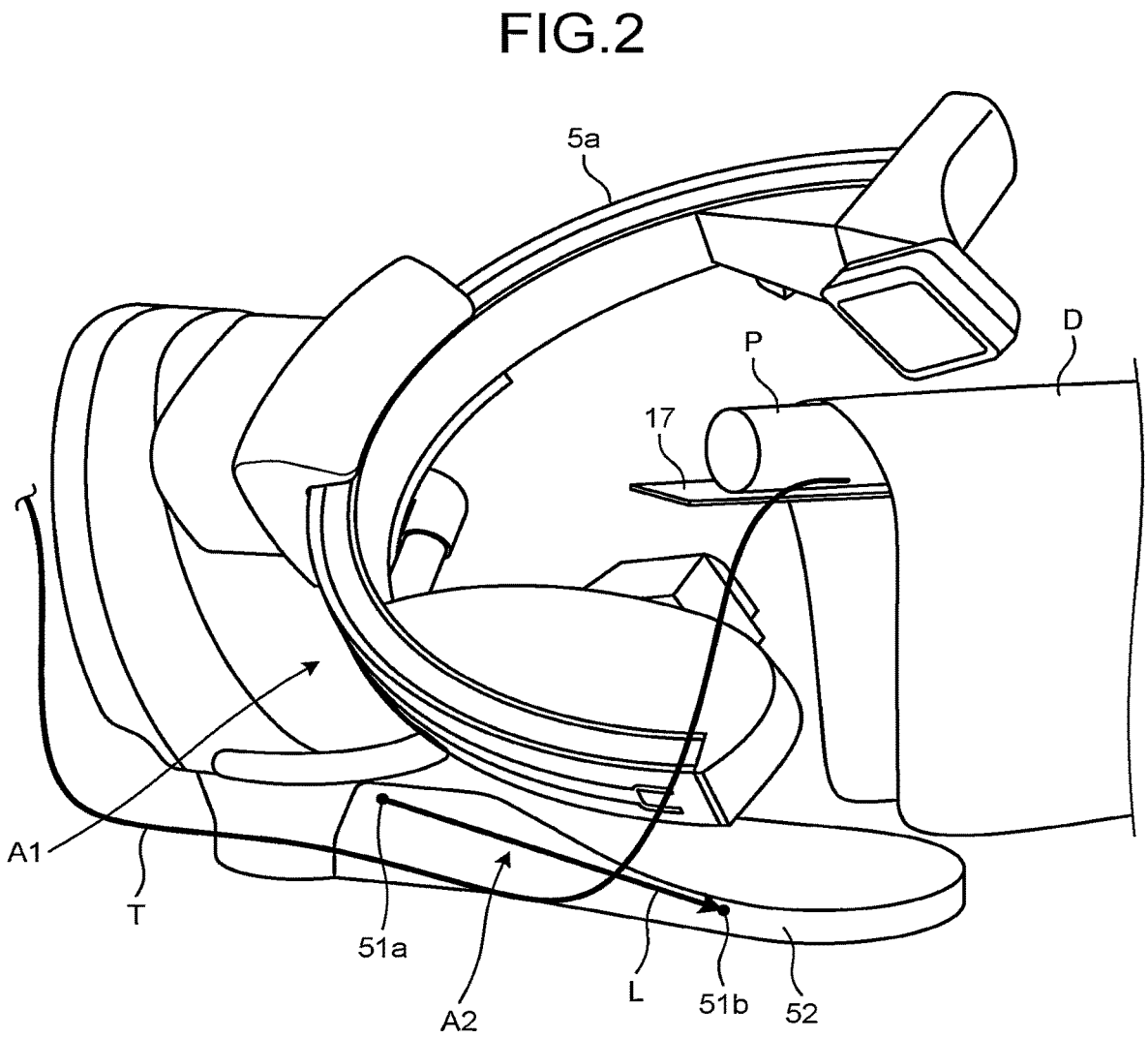
FIG. 2 is a diagram for explaining an example of an optical sensor according to the first embodiment.

In this example, FIG. 2 is a diagram for explaining an example of the optical sensor 51 according to the first embodiment. In FIG. 2, the optical sensor 51 includes a light emitting unit 51*a* and a light receiving unit 51*b*. In the present embodiment, as illustrated in FIG. 2, the light emitting unit 51*a* and the light receiving unit 51*b* are provided on a rotary shaft pedestal 52 of a C-arm 5*a*.

The light emitting unit 51*a* emits laser light L, and the light receiving unit 51*b* receives the laser light L. The optical sensor 51 detects the presence of a person, when the laser light L is blocked and the light receiving unit 51*b* cannot receive the laser light L. For example, by stopping the operation of the C-arm 5*a* when the presence of a person is detected, it is possible to prevent an accident in which the leg of a user such as a doctor operating the C-arm 5*a* or the leg of a person around the C-arm 5*a* is caught by the C-arm 5*a*.

However, for example, when a tube T for blood transfusion is connected to the subject P placed on the couch 17, the laser light L may be blocked by the tube T, and the optical sensor 51 may detect the presence of a person, even if a person is not present. Moreover, for example, if a drape D is covered over the subject P, the laser light L may be blocked by the drape D.

In such a case, the operation of the C-arm 5*a* will be stopped, even though there is little need to stop the operation of the C-arm 5*a*. Moreover, if the operation of the C-arm 5*a* is stopped, for example, to restore the operation, the reset button needs to be pressed, and the user needs to wait until the operation of the apparatus becomes possible again. That is, when the operation of the C-arm 5*a* is stopped even though there is little need to stop the operation of the C-arm 5*a*, the user's operability is degraded.

Furthermore, for example, in the example of FIG. 2, if a person other than the user operating the C-arm 5*a* approaches the vicinity of the location indicated by an arrow A1, the optical sensor 51 may not be able to detect the presence of the person. In this case, the user operating the C-arm 5*a* may operate the C-arm 5*a* without noticing the person around the C-arm 5*a*. Hence, the C-arm 5*a* may come into contact with the other person.

Still furthermore, even if a person approaches the vicinity of the location indicated by an arrow A2, the laser light L may not be blocked. In this case, the leg of the operator of the C-arm 5*a* or the leg of a person around the C-arm 5*a* may be caught by the C-arm 5*a*, by the operation of the C-arm 5*a*. That is, when the presence of a person around the C-arm 5*a* is only detected by the optical sensor, the operability of the arm operated by the user may be degraded.

Therefore, in the X-ray diagnostic system S of the present embodiment, by using an infrared image captured by the infrared camera 200 to determine the interference between the C-arm 5*a* and a person, the operability of the arm operated by the user is improved. The process of using the infrared camera 200 and the infrared image will be described below.

Returning to FIG. 1, the X-ray detection unit 2 detects the X-ray that has passed through the subject P to generate X-ray image data on the basis of the detection results.

Specifically, the X-ray detection unit 2 includes an image data generation unit 20, a flat panel detector (FPD) 21, and a gate driver 22.

The FPD 21 detects the X-ray that has penetrated through the subject P, and transmits the detection results to the image data generation unit 20. For example, the FPD 21 includes a detection film, a pixel capacitance part, a thin film transistor (TFT), and the like.

Under the control of the system control unit 10, the gate driver 22 supplies drive voltage to a gate terminal of the TFT, to read out the charge accumulated in the FPD 21 as an X-ray image signal.

The image data generation unit 20 generates X-ray image data from the detection signal detected by the FPD 21, and stores the generated X-ray image data in an image data memory 13. For example, the image data generation unit 20 performs current/voltage conversion, A/D conversion, and parallel/serial conversion on the detection signal detected by the FPD 21 to generate X-ray image data.

Specifically, the image data generation unit 20 includes a charge/voltage converter 23, an A/D converter 24, and a parallel/serial converter 25.

The charge/voltage converter 23 converts the charge read from the FPD 21 into voltage. The A/D converter 24 converts the output of the charge/voltage converter 23 into a digital signal (digital data). The parallel/serial converter 25 converts the detection signal converted into the digital signal, into a time-series data element.

The image calculation/storage unit 7 corrects and stores the X-ray image data generated by the image data generation unit 20. In the present embodiment, to distinguish between the X-ray image data before and after the correction, the X-ray image data generated by the image data generation unit 20 is referred to as original image data, and the original image data corrected by the image calculation/storage unit 7 is referred to as display X-ray image data.

The image calculation/storage unit 7 includes a memory 11, image calculation circuitry 12, and the image data memory 13.

The memory 11 stores computer programs corresponding to various functions that are read and executed by the image calculation circuitry 12. Moreover, the memory 11 stores data used in various processes performed by the image calculation circuitry 12.

For example, the memory 11 is implemented by a semiconductor memory element such as a random access memory (RAM) and a flash memory, a hard disk, an optical disc, and the like. The memory 11 is an example of a storage unit.

The image calculation circuitry 12 generates display X-ray image data by applying image processing on the original image data generated by the image data generation unit 20, and stores the generated display X-ray image data in the image data memory 13.

The display apparatus 8 includes a display image memory 31, a digital/analog (D/A) converter 32, a display control circuitry 33, and a monitor 34.

The display image memory 31 temporarily stores the display X-ray image data generated by the image calculation circuitry 12 that is read out by the display control circuitry 33.

The D/A converter 32 performs D/A conversion on the display X-ray image data.

The display control circuitry 33 is a processor that controls the monitor 34, and reads the display X-ray image data generated by the image calculation circuitry 12 from the image data memory 13, converts the read display X-ray image data by the D/A converter 32, and displays the converted display X-ray image data on the monitor 34. The display control circuitry 33 is an example of a control unit. Moreover, the display control circuitry 33 may display various graphical user interfaces (GUIs) on the monitor 34.

The monitor 34 displays an X-ray image on the basis of the display X-ray image data, and a GUI for receiving an instruction from the operator. The monitor 34 is implemented by a liquid crystal display, an organic electroluminescence (OEL) display, and the like. The monitor 34 is an example of a display unit.

The operation unit 9 receives various instructions and input of information from the operator. For example, the operation unit 9 is implemented by a trackball, a switch button, a mouse, a keyboard, a touch pad that performs an input operation by touching an operation surface, a touch screen in which a display screen and a touch pad are integrated, a non-contact input circuitry using an optical sensor, a voice input circuitry, and the like. When the operation unit 9 is a touch screen, the monitor 34 and a touch pad may be integrated.

The operation unit 9 is connected to the system control unit 10, and converts the input operation received from the operator into an electrical signal, and outputs the converted electric signal to the system control unit 10. For example, the operation unit 9 receives an operation of turning ON/OFF an automatic parameter setting function of the multi-frequency processing that is performed by the operator. Upon receiving the operation of turning ON/OFF the automatic parameter setting function of the multi-frequency processing, the operation unit 9 sends the received operation contents to the system control unit 10.

Moreover, the operation unit 9 receives an input operation of a user such as imaging conditions and inspection protocols. The operation unit 9 sends the received operation contents to the system control unit 10. Furthermore, the system control unit 10 sends various operation contents obtained from the operation unit 9, to the image calculation circuitry 12.

For example, the imaging conditions include settings on the imaging system, photographing field of view, and magnification rate.

The imaging system is definition or information on the positional relation between the device used for imaging and the subject P, and the positional relation between the devices used for imaging. The positional relation between the device used for imaging and the subject P, and the positional relation between the devices used for imaging are also referred to as imaging geometry. For example, the device used for imaging includes the X-ray tube 15 and the FPD 21.

For example, the imaging system includes source image distance (SID), source skin distance (SSD), the height of the couch 17, and the rotation amount of the holding arm 5.

For example, the magnification rate is specified by the operator by a function referred to as "LiveZoom". LiveZoom is a function that allows the user to zoom in or zoom out the X-ray image displayed on the monitor 34, by operating the operation unit 9.

An examination protocol is information indicating the examination procedures of the X-ray diagnostic apparatus 100, and defines a region to be imaged and the execution procedures of various types of imaging. For example, a plurality of examination protocols are stored in the memory 11 in advance, and the operator may select the examination protocol used for imaging the subject P using the operation unit 9.

In the present specification, the operation unit 9 is not only limited to that including physical operation components such as a mouse and a keyboard. For example, an example of the operation unit 9 includes processing circuitry for electrical signals that receives an electrical signal corresponding to the input operation from an external input device provided separately from the X-ray diagnostic apparatus 100, and that outputs the electrical signal to control circuitry. The operation unit 9 is also referred to as an input interface.

The system control unit 10 integrally controls the X-ray diagnostic apparatus 100. For example, the system control unit 10 includes processing circuitry 101 and a memory 102.

The processing circuitry 101 is a processor that performs an imaging process performed by the X-ray diagnostic apparatus 100. Moreover, the processing circuitry 101 controls the entire X-ray diagnostic apparatus 100, by controlling various components included in the X-ray diagnostic apparatus 100.

More particularly, the processing circuitry 101 includes a first acquisition function 111, a second acquisition function 112, a decision function 113, a display control function 114, and an output function 115. The first acquisition function 111 and the second acquisition function 112 are each an example of an acquisition unit. The decision function 113 is an example of a determination unit, a detection unit, and a control unit. The details of each function will be described below.

For example, the processing circuitry 101 is a processor that implements the function corresponding to each of the computer programs, by reading and executing the computer program from the memory 102. In other words, each circuitry that has read out each computer program has a function corresponding to the read computer program.

The memory 102 stores computer programs corresponding to various functions that are read and executed by the processing circuitry 101. For example, the memory 102 is implemented by a semiconductor memory element such as a RAM and a flash memory, a hard disk, an optical disc, and the like.

In the above description, the "processor" reads and executes a computer program corresponding to each function from the memory 102. However, the embodiment is not limited thereto. For example, the term "processor" refers to circuitry such as a central processing unit (CPU), a graphics processing unit (GPU), an application specific integrated circuit (ASIC), and a programmable logic device (for example, a simple programmable logic device (SPLD), a complex programmable logic device (CPLD), and a field programmable gate array (FPGA)).

For example, when the processor is a CPU, the processor implements the function by reading and executing a computer program stored in the memory 102. On the other hand, when the processor is an ASIC, instead of storing a computer program in the memory 102, the function is directly incorporated into the circuitry of the processor, as logic circuitry. Each processor of the present embodiment is not limited to being configured as single circuitry for each processor, but may also be configured as a single processor by combining a plurality of pieces of independent circuitry to implement the functions. Furthermore, a plurality of components in FIG. 1 may be integrated into a single processor to implement the functions.

Next, the infrared camera 200 will be described. The infrared camera 200 captures an infrared image in which the infrared rays emitted from an object are visualized by sensing the object.

For example, the infrared camera 200 captures an infrared image in which the infrared rays emitted from an object present in the movable range of the holding arm 5 are visualized. The infrared camera 200 may also capture an infrared image in which the infrared rays emitted from an object present in the movable range of the couch 17 are visualized. The infrared camera 200 sends the captured infrared image to the system control unit 10 of the X-ray diagnostic apparatus 100.

It is preferable to install a plurality of the infrared cameras 200 such that blind spots are not created. For example, four infrared cameras 200 are installed at the four corners of the ceiling of the examination room so that the interference between a person (object) and the holding arm 5 can be detected in the movable range of the holding arm 5. The infrared camera 200 capable of capturing 360 degrees may also be installed on the intersection with the main rotary shaft of the holding arm 5 and the like, on the holding arm 5.

Moreover, for example, even if the infrared cameras 200 are installed to cover the movable range of the holding arm 5, in the vicinity of the rotary shaft pedestal 52 that supports the holding arm 5 illustrated in FIG. 2, blind spots are easily created by a medical staff who is working in the examination room other the user operating the holding arm 5, a drape over the subject P, and the like. Therefore, it is preferable to install the infrared cameras 200 such that blind spots are not created in the vicinity of the rotary shaft pedestal 52.

For example, to prevent blind spots from being created in the vicinity of the rotary shaft pedestal 52, it is preferable to install the infrared cameras 200 at the tip end part of the tube of the X-ray tube 15, the rotary shaft pedestal 52, the support of the couch 17, and the like.

Figure 3:
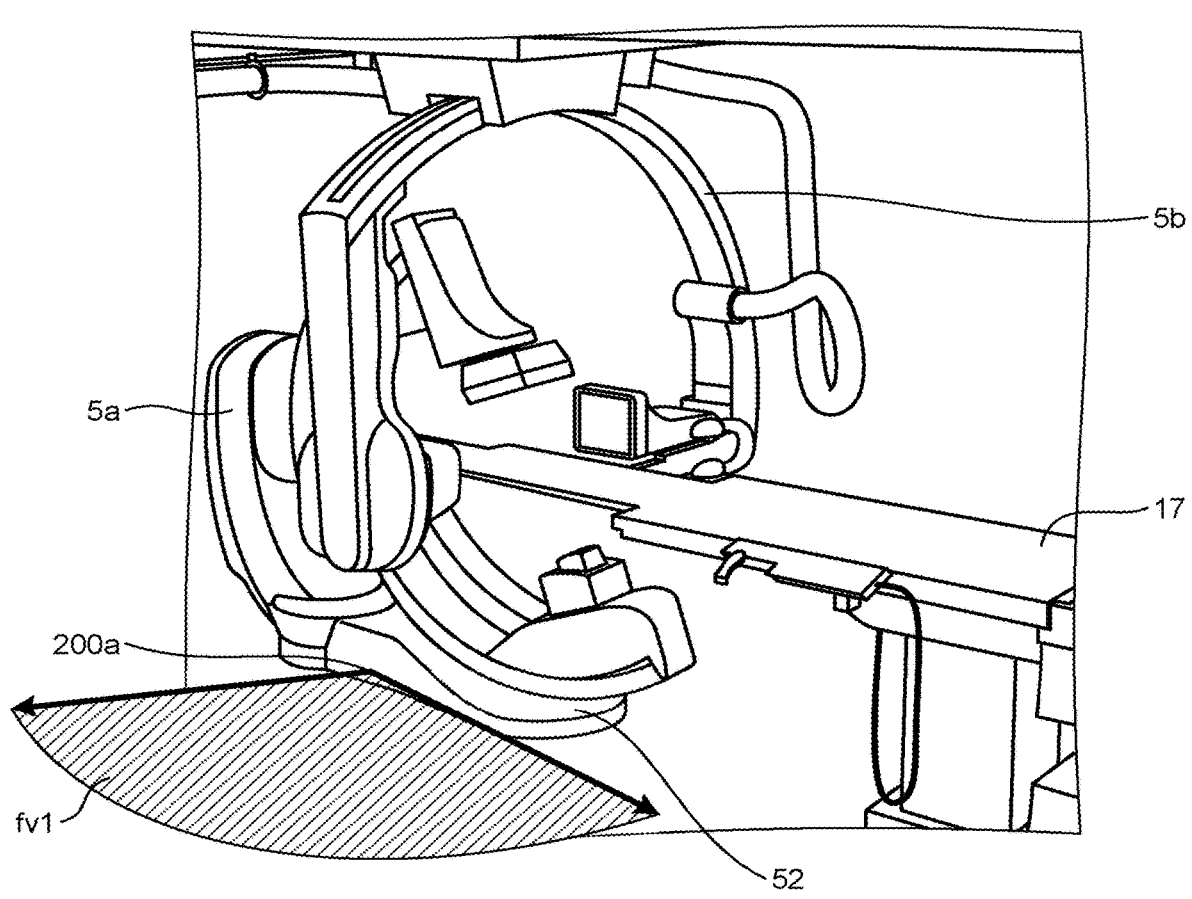
FIG. 3 is a diagram for explaining an example when an infrared camera is installed on a rotary shaft pedestal according to the first embodiment.

In this example, FIG. 3 is a diagram for explaining an example when the infrared camera 200 is installed on the rotary shaft pedestal. For example, as illustrated in FIG. 3, an infrared camera 200a is provided on the rotary shaft pedestal 52 of the C-arm 5a.

Moreover, a field of view fv1 of the infrared camera 200a includes an area around the rotary shaft pedestal 52 of the C-arm 5a. Therefore, the infrared camera 200a can capture an image of an area where blind spots are easily created by a medical staff working in the examination room, a drape over the subject P, and the like. FIG. 3 illustrates the X-ray diagnostic apparatus 100 including an Ω-arm 5b. However, the X-ray diagnostic apparatus 100 may not include the Ω-arm 5b.

Figure 4:
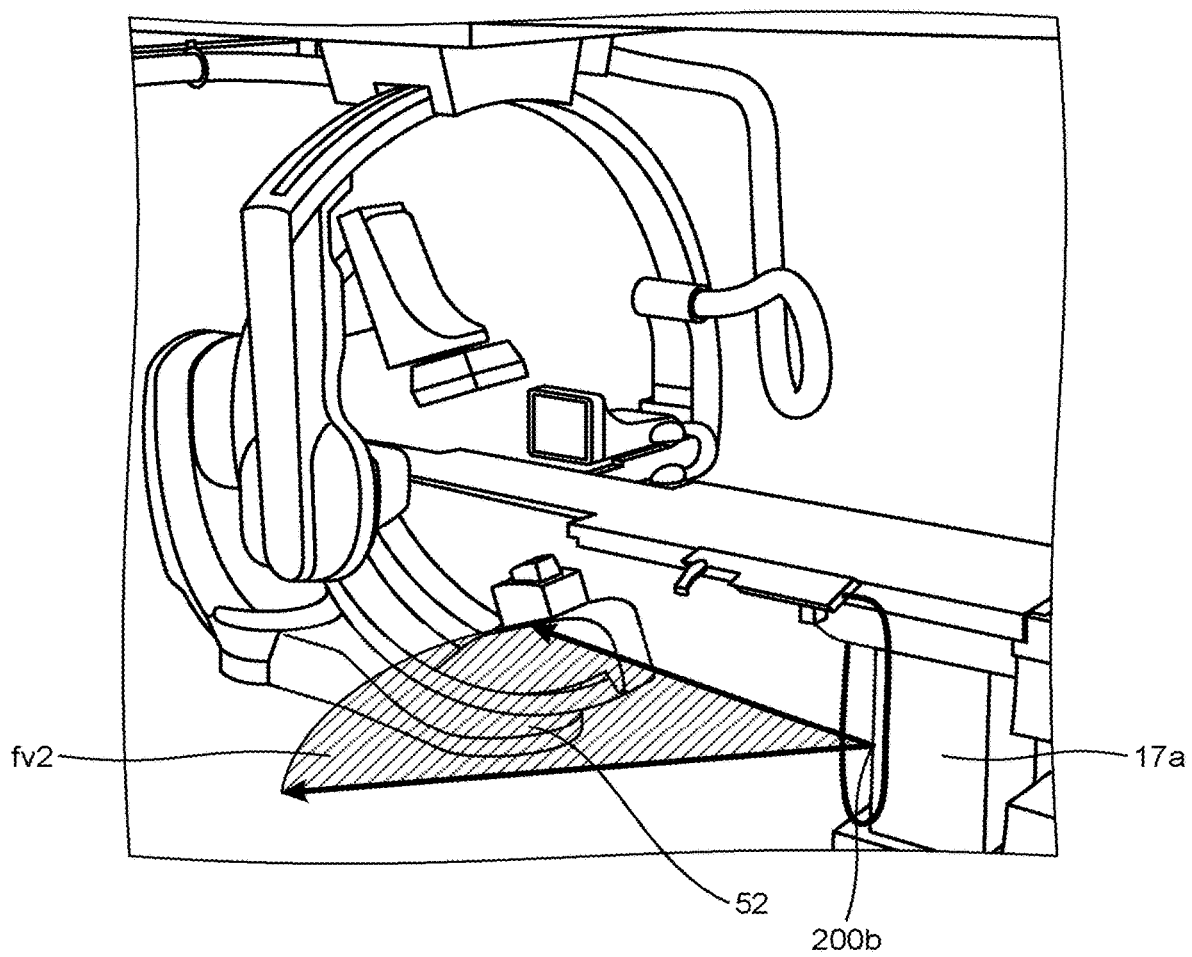
FIG. 4 is a diagram for explaining an example when an infrared camera is installed on a support of a couch according to the first embodiment.

Moreover, FIG. 4 is a diagram for explaining an example when the infrared camera 200 is installed on the support of the couch 17. For example, as illustrated in FIG. 4, an infrared camera 200b is provided on a support 17a of the couch 17. A field of view fv2 of the infrared camera 200b includes a portion difficult to see from the surrounding area, when a drape is covered over the subject P. Therefore, the infrared camera 200b can also capture an infrared image of such a portion. If the support 17a rotates, the infrared cameras 200 may also be provided on the support 17a.

Next, with reference to FIG. 1, each function of the processing circuitry 101 in the present embodiment will be described.

The first acquisition function 111 acquires the sensing results sent from the optical sensor 51. For example, as the sensing results, the first acquisition function 111 acquires the detection results whether the laser light L is received.

The second acquisition function 112 acquires the infrared image sent from the infrared camera 200. For example, the second acquisition function 112 acquires the infrared image captured by each of the infrared cameras 200 installed in the examination room and the X-ray diagnostic apparatus 100, from each of the infrared cameras 200. The infrared image may be a still image or a moving image. Moreover, the first acquisition function 111 and the second acquisition function 112 may be configured as a single functional part.

The decision function 113 determines the classification of the object present in the movable range of the movable unit of the X-ray diagnostic apparatus 100, on the basis of the infrared image. Furthermore, the decision function 113 determines the control contents to be performed by the X-ray diagnostic apparatus 100, on the basis of the results of classification determination.

Still furthermore, the mechanism control unit 6 or the system control unit 10 controls the operation of X-ray imaging according to the control contents determined by the decision function 113. In other words, the decision function 113 cooperatively works with the mechanism control unit 6, the system control unit 10, and the like, and controls the operation of X-ray imaging according to the X-ray imaging, on the basis of the determination results of the classification of the object.

Specifically, the decision function 113 determines the classification of the object in the infrared image, on the basis of the temperature distribution of the area in the infrared image. For example, the decision function 113 determines whether an object in the infrared image is the type of object with which interference should be avoided (for example, such as a person) or the type of object with which interference need not necessarily be avoided (for example, such as a drape). The type of object with which interference should be avoided is an object that needs to be prevented from being brought into contact with the holding arm 5, and is an example of an object to be avoided.

As an example, the decision function 113 determines an object corresponding to a heat source area indicating a predetermined temperature zone (for example, a temperature range indicating the body temperature of human) in an infrared image, as the type of object with which interference should be avoided. On the other hand, the decision function 113 determines a heat source area indicating the temperature zone other than the above, as the type of object with which interference need not necessarily be avoided.

Moreover, for example, on the basis of the detection of a heat source area determined as the type of object with which interference should be avoided, the decision function 113 determines to maintain or change the driving speed of the holding arm 5, as the control contents to be performed by the X-ray diagnostic apparatus 100.

As an example, if a heat source determined as the type of object with which interference should be avoided is detected in the movable range of the holding arm 5, the decision function 113 determines the control to stop driving (set the driving speed to zero) or to reduce the driving speed of the holding arm 5, as control to be performed.

On the other hand, if a heat source determined to be other than the type of object with which interference should be avoided is detected in the movable range of the holding arm 5, the decision function 113 does not perform control of stop driving the holding arm 5 to avoid contact. In this process, the decision function 113 may maintain or reduce the driving speed of the holding arm 5.

Hereinafter, with reference to FIG. 5 to FIG. 7, operation of the decision process of the control contents will be described. In the following, the object to be controlled is the holding arm 5. However, the object to be controlled may also be other movable regions such as the couch 17.

First, the decision function 113 determines whether an object is detected around the holding arm 5, from the sensing results acquired by the first acquisition function 111. Specifically, when the detection results indicating that the laser light L cannot be received by the first acquisition function 111 is acquired, the decision function 113 determines that an object is detected.

Next, the decision function 113 determines the classification of the object in the infrared image acquired by the second acquisition function (whether the object is the type with which interference should be avoided, or the type with which interference need not necessarily be avoided). Specifically, the decision function 113 determines the heat source area producing heat exceeding a threshold value in the infrared image, as the type of object with which interference should be avoided, and determines the heat source area other than the heat source area described above, as the type of object with which interference need not necessarily be avoided.

More specifically, the decision function 113 sets a threshold range (for example, between 35 degrees Celsius and 40 degrees Celsius), on the basis of the average body temperature of human (approximately 37 degrees Celsius). Then, if there is an area in which the temperature has a value within the threshold range in the infrared image acquired by the second acquisition function, the decision function 113 determines that the heat source area indicated by the area, as the type of object with which interference should be avoided.

For example, if the threshold range is set between 35 degrees Celsius and 40 degrees Celsius, the temperature of the components in the X-ray diagnostic apparatus 100 such as a tube of the X-ray tube 15 may have a value within the threshold range. Moreover, for example, even if a drape is covered over the subject P, the heat emitted by the subject P may not be blocked, and the temperature at the location where the subject P is placed may have a value within the threshold range. In such a case, it is preferable to exclude the tube of the X-ray tube 15 and the subject P from the object to be detected (the type of object with which interference should be avoided), because the tube of the X-ray tube 15 and the subject P do not interfere with the holding arm 5.

Thus, for example, the decision function 113 obtains the positional information on the portion where the temperature may have a value within the threshold range such as a tube of the X-ray tube 15 and the couchtop (a portion where the subject P is placed) of the couch 17.

In this example, the positional information on each part of the X-ray diagnostic apparatus 100 is managed by the system control unit 10. With reference to the positional information on each part of the X-ray diagnostic apparatus 100 stored in the memory 102 and the like by the system control unit 10, the decision function 113 obtains the positional information on the portion where the temperature may have a value within the threshold range.

Moreover, the decision function 113 specifies the position corresponding to such a portion in the infrared image from the positional information. Then, the decision function 113 may set the specified location in the infrared image as an object not to be detected.

Figure 5:
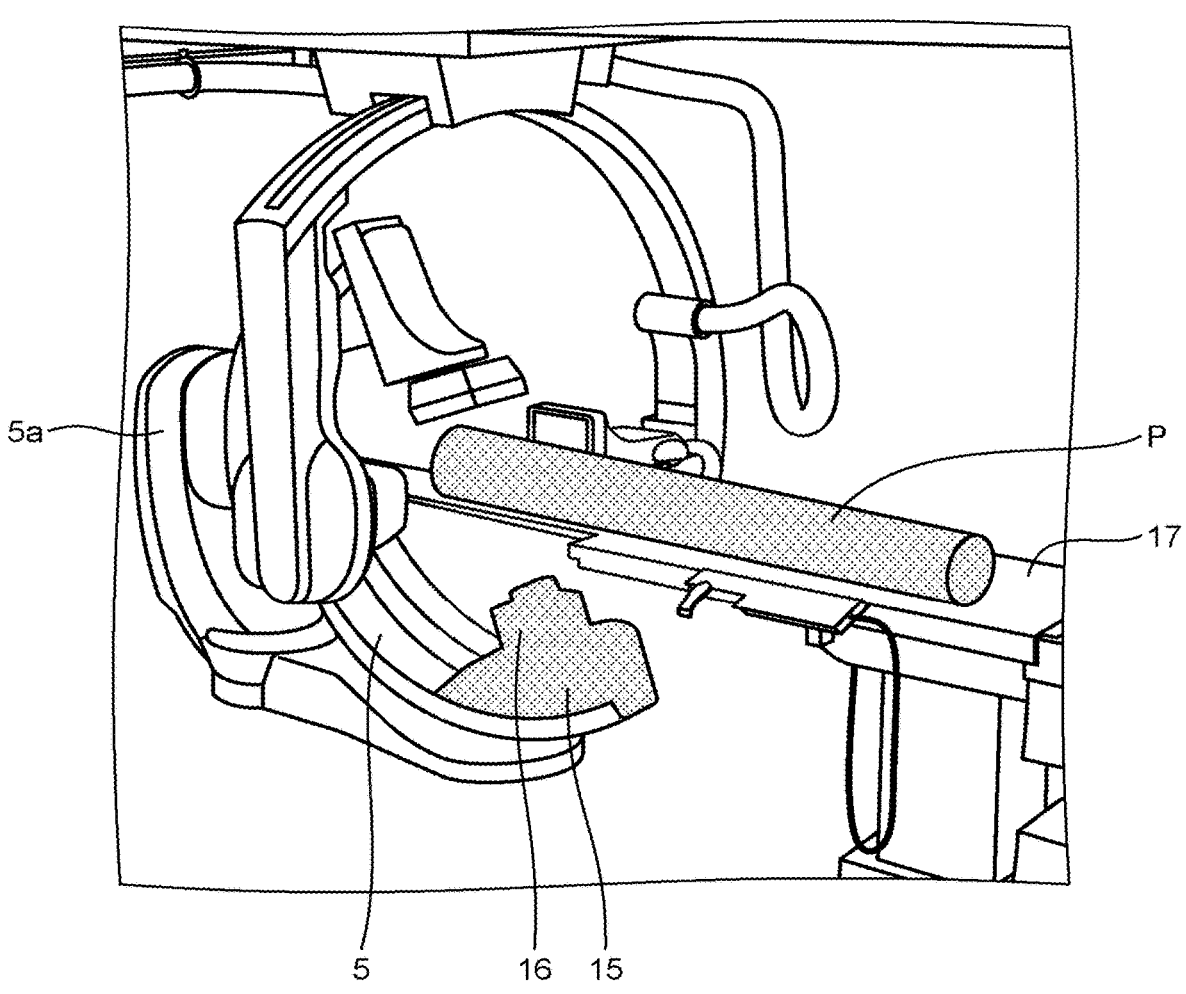
FIG. 5 is a diagram illustrating an example of a portion not to be detected according to the first embodiment.

In this example, FIG. 5 is a diagram illustrating an example of a portion not to be detected. For example, if the temperature of the X-ray tube 15, the X-ray diaphragm 16, and a portion of the couch 17 where the subject P is placed each have a value within the threshold range, as described above, the decision function 113 specifies the locations of the X-ray tube 15, the X-ray diaphragm 16, and the portion of the couch 17 where the subject P is placed in the infrared image.

In FIG. 5, the patterned portions represent the X-ray tube 15, the X-ray diaphragm 16, and the portion of the couch 17 where the subject P is placed. The decision function 113 sets the locations in the infrared image corresponding to such portions, as objects not to be detected.

Moreover, the decision function 113 may also perform a process of setting a portion the positional relation of which with a specific portion (for example, the tube of the X-ray tube 15) of the holding arm 5 exceeds a predetermined range (for example, within a radius of n meters around the tube), as an object not to be detected.

For example, the decision function 113 specifies the location of the tube of the X-ray tube 15 in the infrared image on which the tube of the X-ray tube 15 is illustrated, from the positional information described above. Next, on the basis of the corresponding relation between the distance in the real space and the distance in the infrared image, the decision function 113 specifies the area within a radius of n meters around the tube in the infrared image.

In this case, it is also possible to say that the decision function 113 is detecting the positional relation between the heat source and the tube of the X-ray tube 15 (holding arm 5). Therefore, the decision function 113 according to the present embodiment is an example of a detection unit.

Next, the decision function 113 determines the control to be performed, from the detection results based on the sensing results of the optical sensor 51 and the detection results based on the infrared image including the determination of the classification of the object. For example, with reference to a decision table for determining the control corresponding to the state of interference between the holding arm 5 and a person, the decision function 113 determines the control contents to be performed.

The decision table is a data table in which the detection results based on the sensing results of the optical sensor 51, the detection results based on the infrared image, and the control to be performed are associated with each other. In this example, FIG. 6 is a diagram illustrating an example of a decision table 102a. The decision table 102a in FIG. 6 is stored in the memory 102.

In the decision table 102a, "Optical Sensor" indicates whether an object is detected by the optical sensor 51, "Temperature" indicates whether a heat source area determined as the type of object with which interference should be avoided is detected, and "Control" indicates control to be performed. For example, the first line in FIG. 6 indicates that when the optical sensor 51 detects an object, and when the infrared camera 200 detects a heat source area determined as the type of object with which interference should be avoided, the operation of the holding arm 5 is stopped. This is because there is a high possibility that a person is present around the holding arm 5.

Moreover, the second line in FIG. 6 indicates that when the optical sensor 51 detects an object, but when the infrared camera 200 does not detect a heat source area determined as the type of object with which interference should be avoided, the user is notified with an alert indicating that a person may be present around the holding arm 5. In this case, notification of an alert is an example of a control for operating the X-ray imaging and for preventing the movable unit from coming into contact with the object to be avoided.

This is because although the optical sensor 51 detects an object, the infrared camera 200 does not detect a heat source area determined as the type of object with which interference should be avoided, there is a high possibility that the laser light L is blocked by an object such as a drape covering the subject P and the like. In this case, because there is little need to stop the holding arm 5, a response is made by issuing an alert. There is also a possibility that a medical staff other than the user may be working while being hidden by a drape. However, even in such a case, it is considered sufficient enough to notify the user with an alert and warn the user to move the holding arm 5 with caution.

Furthermore, the third line in FIG. 6 indicates that when the optical sensor 51 does not detect an object, but when only the infrared camera 200 detects a heat source area determined as the type of object with which interference should be avoided, control is performed to reduce the driving speed of the holding arm 5. This is because the heat source area determined as the type of object with which interference should be avoided is present around the holding arm 5, there is a high possibility that a person is present around the holding arm 5. However, because the optical sensor 51 does not detect an object, it is possible to consider that the person is present at a location slightly away from the holding arm 5. Therefore, it is considered there is little need to immediately stop the holding arm 5.

Still furthermore, the fourth line in FIG. 6 indicates that when the optical sensor 51 does not detect an object, and when the infrared camera 200 does not detect a heat source area determined as the type of object with which interference should be avoided, no particular control takes place. This is because there is a small possibility that a person is present around the holding arm 5.

The user may be able to change the contents of the decision table 102a. For example, in the second line in FIG. 6, when the optical sensor 51 detects an object, but when the infrared camera 200 does not detect a heat source area determined as the type of object with which interference should be avoided, the user may change the "Control" such that not only an alert is notified, but also a process of reducing the speed of the holding arm 5 is performed.

Still furthermore, because there are a plurality of movable units in the holding arm 5, the decision table 102a may define the control contents for each of the movable units. In this example, FIG. 7 is a diagram for explaining a plurality of movable units of the C-arm 5a according to the first embodiment.

Figure 7:
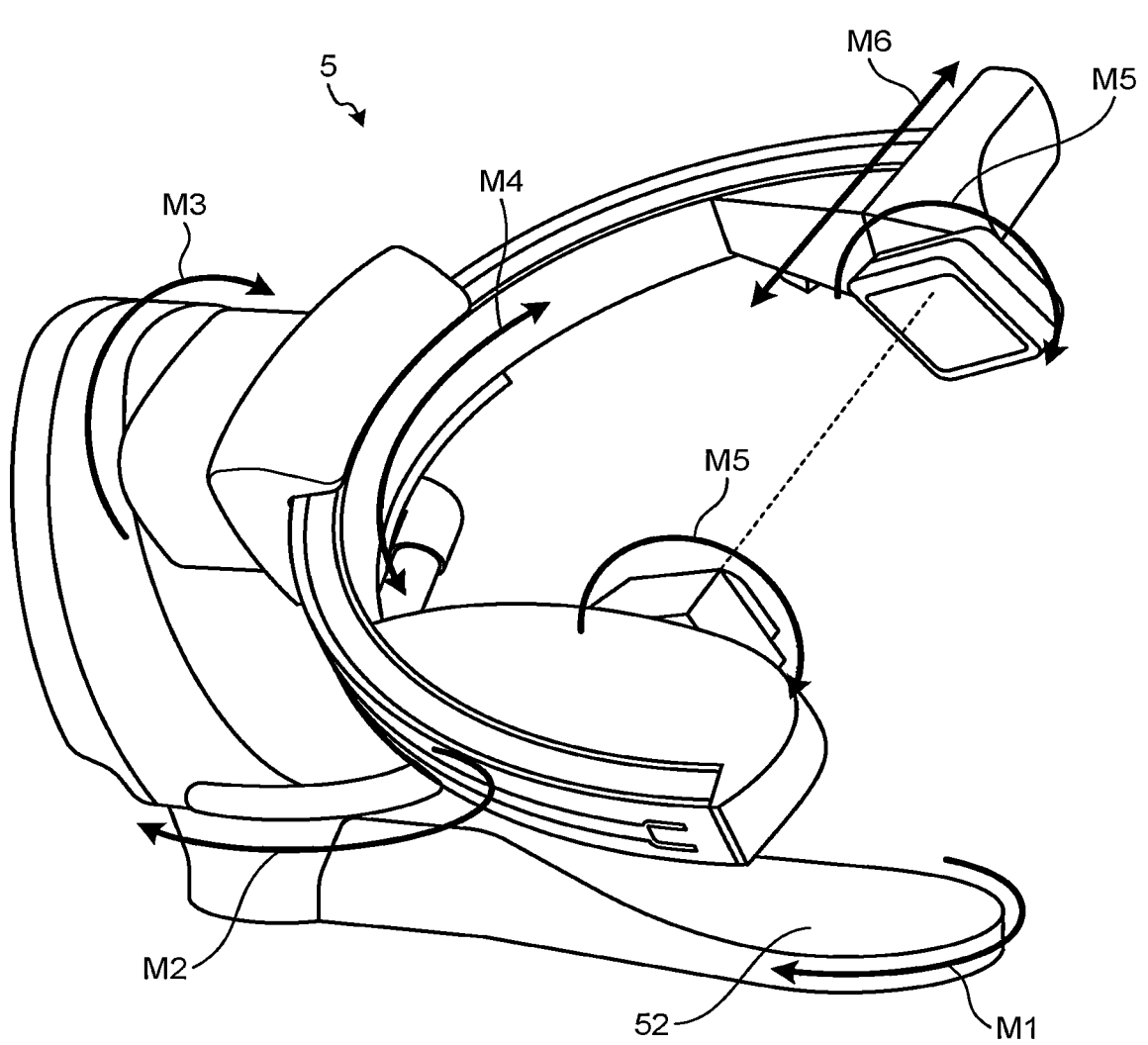
FIG. 7 is a diagram for explaining a plurality of movable units of a C-arm according to the first embodiment.

In FIG. 7, a movable unit M1 is a movable unit that performs the rotational movement of the C-arm 5a around the floor rotary shaft. Moreover, a movable unit M2 is a movable unit that performs the rotational movement of the C-arm 5a around the rotary shaft of the support of the arm. Furthermore, a movable unit M3 is a movable unit that performs the rotational movement of the C-arm 5a around the main rotary shaft of the arm. Still furthermore, a movable unit M4 is a movable unit that moves the C-arm 5a around the rotary shaft of the arm slide in a sliding manner.

Still furthermore, a movable unit M5 is a movable unit that performs the rotational movement of the X-ray diaphragm 16 and the FPD 21 around the rotational axes of the X-ray diaphragm 16 and the FPD 21. Still furthermore, a movable unit M6 is a movable unit that moves the FPD 21 in the vertical direction.

For example, in the decision table 102a, a relation between the detection results and the control may also be defined, such as "When the optical sensor 51 does not detect an object, but when only the infrared camera 200 detects a heat source area determined as the type of object with which interference should be avoided, the movable unit M3 is controlled to stop driving, but the other movable units are controlled to reduce speed".

In the above, the decision function 113 determines the control contents to be performed using the detection results of the presence of an object based on the sensing results of the optical sensor 51. However, the decision function 113 may also determine the control contents to be performed only using the detection results of a heat source area determined as the type of object with which interference should be avoided, based on the infrared image. In this case, for example, the decision function 113 may also determine the control contents on the basis of the presence of a heat source within a radius of n meters from the tube of the X-ray tube 15.

Returning to FIG. 1, the description will be continued. The display control function 114 performs control to cause the display apparatus 8 and the like to display various types of information. For example, when the decision function 113 determines to perform control of notifying the user with an alert, the display control function 114 cooperatively works with the display control circuitry 33, and causes the monitor 34 to display a warning message warning the user to check the presence of a person around the holding arm 5.

In this case, the display control function 114 may also cause the monitor 34 to display information indicating the location (hereinafter, may be referred to as an interference portion) of the heat source area that has caused the display control function 114 to perform control of notifying the user with an alert.

In this case, for example, the display control function 114 specifies the location in the real space corresponding to the location of the heat source area (an area with the temperature within the threshold range) that is determined as the type of object with which interference should be avoided in the infrared image, from the positional information described above. Next, the display control function 114 performs a process of superimposing and displaying a mark indicating the location, on the illustration representing the X-ray diagnostic apparatus 100 and the surrounding space, and the like.

Moreover, in addition to the monitor 34, the display control function 114 may also cause a monitor or the like for controlling the infrared camera 200 provided in the examination room or the like (may also be in a control room or the like outside the examination room) to display the interference portion. Furthermore, when a heat source area determined as the type of object with which interference should be avoided is not detected from the infrared image, but when the user is notified with an alert, the display control function 114 may cause the monitor 34 or the like to display the location of the optical sensor 51 as an interference portion, in addition to the information indicating that the optical sensor 51 has detected an object.

In the present embodiment, the user is notified with an alert when the display control function 114 causes the monitor 34 to display a warning message. However, the notification method is not limited to the display. For example, the processing circuitry 101 may also notify the user with an alert by causing a speaker or the like to output a warning sound.

The output function 115 outputs various types of information. For example, when the decision function 113 determines to perform control of stop driving the holding arm 5, the output function 115 sends a command to the mechanism control unit 6 to stop driving the holding arm 5 according to the decision.

Upon receiving the command sent by the output function 115, the mechanism control unit 6 controls the holding arm moving mechanism 41 to stop driving the holding arm 5. Even if the decision function 113 determines to perform a control to reduce the driving speed of the holding arm 5, the output function 115 performs the similar process.

When the mechanism control unit 6 has controlled the driving of the holding arm 5 and the like according to the decision made by the decision function 113, the display control function 114 described above may also cause the monitor 34 or the like to display the location of the heat source area that has caused the mechanism control unit 6 to perform the control, as an interference portion.

Figure 8:
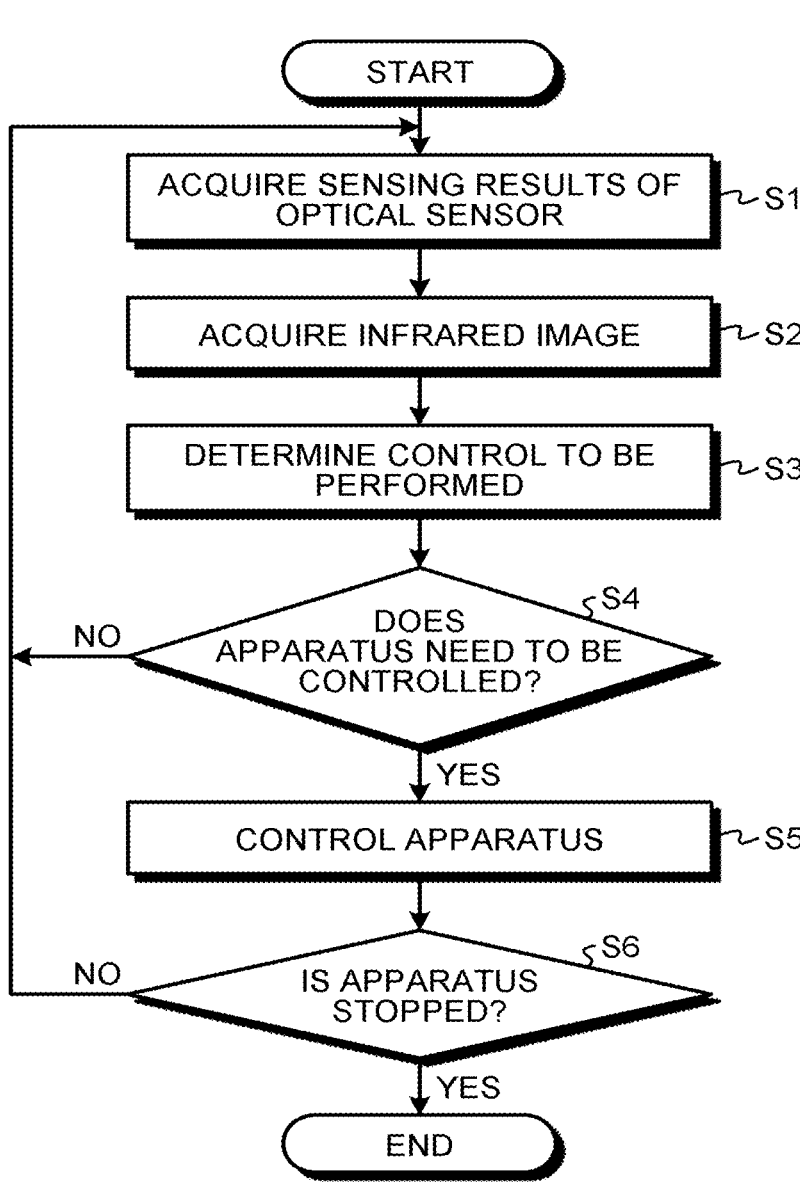
FIG. 8 is a flowchart illustrating an example of a process performed by the X-ray diagnostic apparatus according to the first embodiment.

Next, a process performed by the X-ray diagnostic apparatus 100 according to the present embodiment will be described. FIG. 8 is a flowchart illustrating an example of a process performed by the X-ray diagnostic apparatus 100 according to the first embodiment.

First, the first acquisition function 111 acquires the sensing results sent by the optical sensor 51 (step S1). For example, the first acquisition function 111 acquires information indicating whether the light receiving unit 51*b* has received the laser light L, as a sensing result. In FIG. 8, the acquisition of sensing results is described as the process at step S1. However, it is considered that the first acquisition function 111 continuously acquires the sensing results sent by the optical sensor 51, while the holding arm 5 is being driven.

Next, the second acquisition function 112 acquires the infrared image sent from the infrared camera 200 (step S2). For example, the second acquisition function 112 acquires an infrared image from each of the infrared cameras 200 installed in the examination room and the X-ray diagnostic apparatus 100. In FIG. 8, the acquisition of the infrared image is described as the process at step S2. However, it is considered that the second acquisition function 112 continuously acquires the infrared images sent from the infrared camera 200, while the holding arm 5 is being driven.

Next, on the basis of the sensing results of the optical sensor 51 obtained at step S1 and the infrared images obtained at step S2, the decision function 113 determines the control to be performed (step S3).

For example, the decision function 113 determines whether an object is detected, from the sensing results of the optical sensor 51 obtained at step S1. Moreover, the decision function 113 determines whether a heat source area determined as the type of object with which interference should be avoided is detected from the infrared image obtained at step S2. Then, with reference to the decision table 102*a* stored in the memory 102, the decision function 113 determines the control corresponding to a combination of the detection of an object and the detection of a heat source area determined as the type of object with which interference should be avoided, as control to be performed.

Next, the output function 115 determines whether the control determined at step S3 involves mechanism control (step S4). For example, when the determined control is to notify the user with an alert, the output function 115 determines that the determined control does not involve mechanism control. On the other hand, when the determined control is to stop driving or reduce the speed of the holding arm 5, the output function 115 determines that the determined control involves mechanism control.

When the determined control does not involve mechanism control (No at step S4), the determined control is performed, and the process returns to step S1. On the other hand, when the determined control involves mechanism control (Yes at step S4), the output function 115 outputs a command urging the mechanism control unit 6 to control the mechanism according to the decision.

Next, the mechanism control unit 6 that has received the command controls the mechanism, and performs the control determined at step S3 (step S5). For example, if the control to be performed is to stop driving the holding arm 5, the mechanism control unit 6 controls the holding arm moving mechanism 41 to stop driving the holding arm 5.

Next, the first acquisition function 111 checks whether a portion of the X-ray diagnostic apparatus 100 serving as the object to be controlled is stopped (step S6). For example, when the holding arm 5 is the object to be controlled, the first acquisition function 111 checks whether the holding arm 5 is stopped. When a portion serving as the object to be controlled is not stopped (No at step S6), the first acquisition function 111 continues the acquisition process of the sensing results of the optical sensor 51 (the process returns to step S1). On the other hand, when a portion serving as the object to be controlled is stopped, the present process is terminated.

As described above, on the basis of the infrared image captured by the infrared camera 200, the X-ray diagnostic system S according to the first embodiment determines the classification of the object in the infrared image, and determines the control to be performed by the X-ray diagnostic apparatus 100 with which the classification is determined based on the determination results.

Consequently, for example, an object that does not produce heat exceeding a predetermined value can be determined as the type of object (person) with which interference need not necessarily be avoided, even if the object approaches the holding arm 5 of the X-ray diagnostic apparatus 100. Therefore, there is no need to stop driving the holding arm 5. That is, with the X-ray diagnostic system S according to the first embodiment, it is possible to improve the operability of the X-ray diagnostic apparatus by the user.

Moreover, the X-ray diagnostic system S according to the first embodiment includes the optical sensor 51, and determines the control to be performed by the X-ray diagnostic apparatus 100, on the basis of the sensing results of the optical sensor 51 and the detection of a heat source area determined as the type of object with which interference should be avoided in the infrared image.

Consequently, for example, in a case when an object is detected by the optical sensor 51, but when a heat source area determined as the type of object with which interference should be avoided is not detected from the infrared image, it is possible to determine that there is a high possibility that the optical sensor 51 has reacted to an object other than a person. Moreover, for example, when an object is not detected by the optical sensor 51, but when a heat source area determined as the type of object with which interference should be avoided can be detected from an infrared image, it is possible to determine that even if a person is present in the vicinity of the holding arm 5, there is a high possibility that the person is not present close enough to immediately stop driving the holding arm 5. In this manner, the X-ray diagnostic system S according to the first embodiment can not only estimate whether an object interferes with the holding arm 5, but can also estimate whether the object is most likely a person, and if a person is present, can estimate whether the person is far away, nearby, or the like. Moreover, the control of the X-ray diagnostic apparatus 100 can be changed accordingly. That is, with the X-ray diagnostic system S according to the first embodiment, it is possible to change the control in multiple stages according to the degree of estimated interference, such as reducing the driving speed of the holding arm 5 when a person is assumed to be far away, and stop driving the holding arm 5 when a person is assumed to be nearby.

Second Embodiment

In the first embodiment described above, a form in which the decision function 113 uses an infrared image to determine the detection of a heat source area determined as the type of object with which interference should be avoided has been described. In a second embodiment, a form in which an infrared image is further used for identifying the shape of the heat source area in the infrared image will be described.

In the following, points different from the embodiment described above will be mainly described, and detailed description of points common to the contents already described above will be omitted. Moreover, each of the embodiments described below may be implemented individually, or in combination as appropriate.

Figure 9:
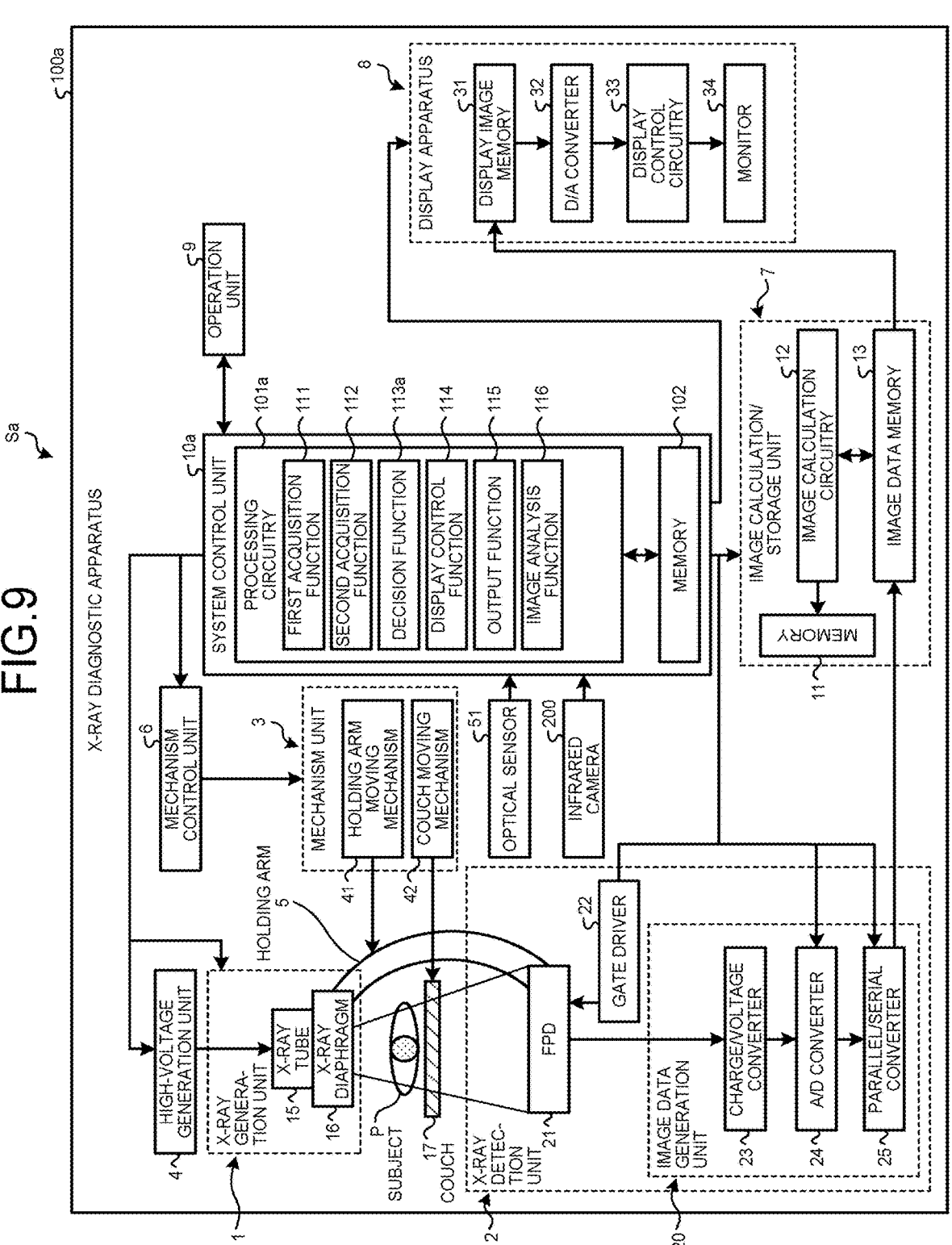
FIG. 9 is a block diagram illustrating an example of a configuration of an X-ray diagnostic apparatus according to a second embodiment.

Hereinafter, a configuration of a system control unit 10a of an X-ray diagnostic apparatus 100a of an X-ray diagnostic system Sa according to the second embodiment will be described. FIG. 9 is a block diagram illustrating an example of a configuration of the X-ray diagnostic apparatus 100a according to the second embodiment.

Processing circuitry 101a of the system control unit 10a of the X-ray diagnostic apparatus 100a according to the second embodiment includes the first acquisition function 111, the second acquisition function 112, a decision function 113a, the display control function 114, the output function 115, and an image analysis function 116. Because the first acquisition function 111, the second acquisition function 112, the display control function 114, and the output function 115 are the same as those in the first embodiment, the description thereof will be omitted.

First, the image analysis function 116 will be described. The image analysis function 116 analyzes an infrared image. For example, the image analysis function 116 analyzes the infrared image acquired by the second acquisition function 112, and identifies the shape of the heat source area detected in the infrared image. Because a known technique can be used for analyzing an image, the description thereof will be omitted.

Figure 10:
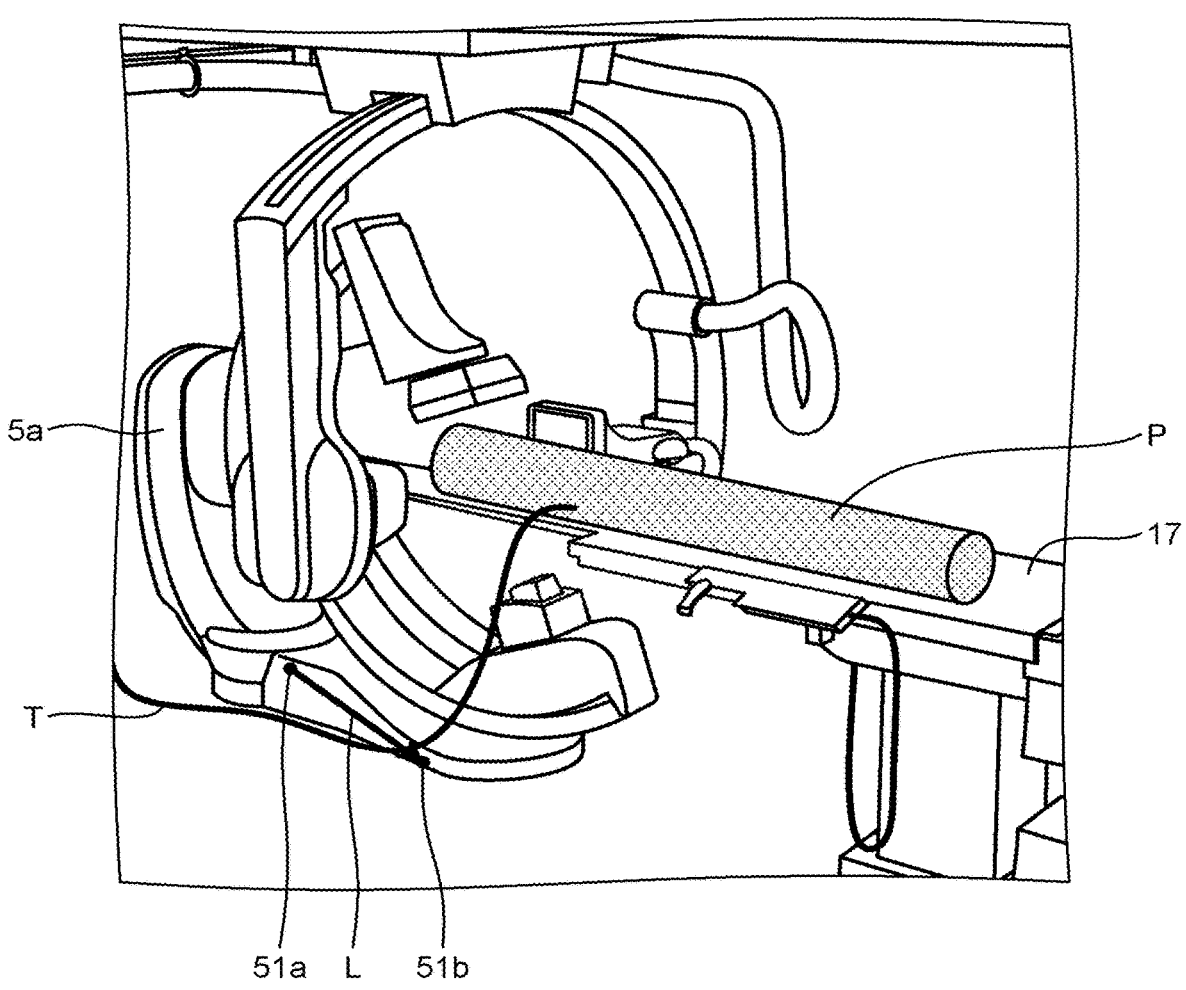
FIG. 10 is a diagram for explaining an example of a tube connected to a subject according to the second embodiment.

Hereinafter, an image analysis process will be described with reference to FIG. 10 and FIG. 11. FIG. 10 is a diagram for explaining an example of a tube connected to the subject P. In the present specification, the tube indicates a tube for giving blood transfusion to a patient and the like. Moreover, the tube may also be a tube for administering medicine and the like used in examination such as contrast medium to a patient.

When blood transfusion is given to the subject P, in general, blood product is warmed up to about body temperature before being given to the subject P. The same also applies when medicine such as contrast medium is given to the subject P. Therefore, as illustrated in FIG. 10, when the hanging tube blocks the laser light L, the optical sensor 51 detects an object, and a heat source area determined as the type of object with which interference should be avoided is also detected from the infrared image.

That is, when control is determined on the basis of the sensing results of the optical sensor 51 and the detection of a heat source area determined as the type of object with which interference should be avoided, there may be an erroneous detection of a person present around the C-arm 5a, and may cause the C-arm 5a to stop driving.

Thus, the image analysis function 116 analyzes the infrared image, and identifies the shape of the heat source area detected in the infrared image. In this example, FIG. 11 is a diagram illustrating an example of an infrared image. In FIG. 11, the image analysis function 116 analyzes the infrared image, and identifies the presence of a heat source with an elongated (tubular) shape and a heat source having a shape that can be estimated as the X-ray tube 15 and the X-ray diaphragm 16. The image analysis function 116 is an example of a recognition unit.

For example, when the C-arm 5a is an object to be controlled, the X-ray tube 15 and the X-ray diaphragm 16 do not interfere with the C-arm 5a. Hence, when the image analysis function 116 has identified a heat source having a shape that can be estimated as the X-ray tube 15 and the X-ray diaphragm 16 in the infrared image, the heat source may be excluded from the object to be detected.

Returning to FIG. 9, the description will be continued. The decision function 113a determines the control to be performed on the basis of the detection of an object by the optical sensor 51, the detection of a heat source area determined as the type of object with which interference should be avoided using an infrared image, and the shape of the object in the infrared image.

As an example, the decision function 113a refers to a decision table 102b in which the detection of an object by the optical sensor 51, the detection of a heat source area determined as the type of object with which interference should be avoided using an infrared image, the shape of the object in the infrared image, and the control are associated with each other. Then, the decision function 113*a* determines the control corresponding to the detection of an object by the optical sensor 51, the detection of a heat source area determined as the type of object with which interference should be avoided using an infrared image, and the shape of the object identified in the infrared image, as control to be performed.

Similar to the first embodiment, it is considered that the decision function 113*a* determines the classification of the object, on the basis of the temperature range of the heat source area. However, the decision function 113*a* may also determine the classification of the object itself (person, tube, drape, and the like), from the shape of the heat source area within a predetermined temperature range.

In this case, for example, with reference to determination information such as a determination table in which the classification of the object and the necessity to avoid the interference are associated with each other and stored, the decision function 113*a* determines whether the object is the type of object with which interference should be avoided, on the basis of the necessity to avoid interference, corresponding to the determined classification of the object.

Moreover, in the above case, according to the determined classification of the type of object with which interference should be avoided, the decision function 113*a* may determine to maintain or change the driving speed of the movable unit as the control content.

As an example, when the classification of the type of object with which interference should be avoided is other than a person, the decision function 113*a* may determine to maintain or reduce the driving speed of the movable unit as the control content. On the other hand, when the classification of the type of object with which interference should be avoided is a person, the decision function 113*a* may determine to stop driving the movable unit as the control content.

Figures 11, 12:
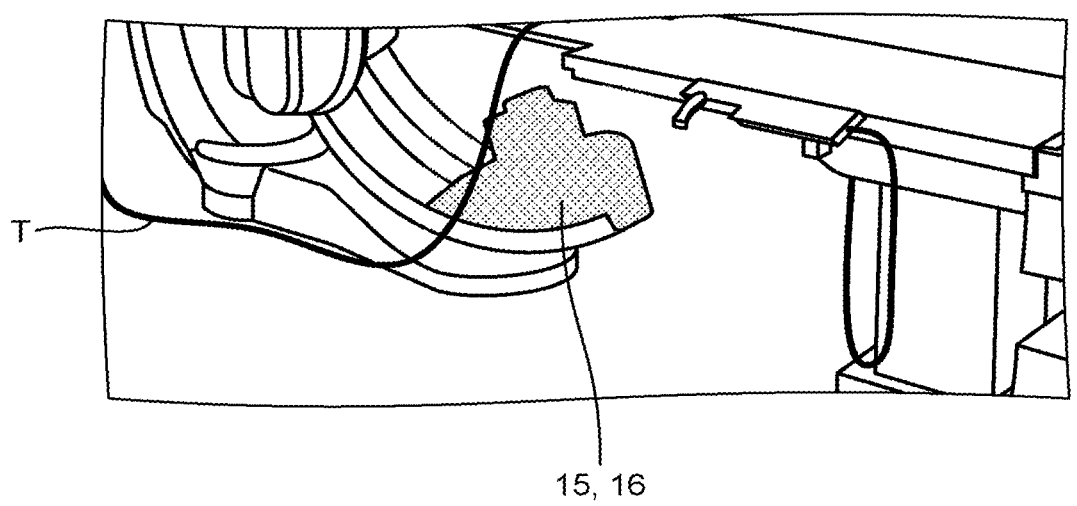
FIG. 11 is a diagram illustrating an example of an infrared image according to the second embodiment.
FIG. 12 is a diagram illustrating an example of a decision table according to the second embodiment.

In this example, FIG. 12 is a diagram illustrating an example of the decision table 102*b* according to the second embodiment. "Shape" in the decision table 102*b* indicates the shape of the heat source area determined as the type of object with which interference should be avoided in the infrared image identified by the image analysis function 116. Moreover, "Detection" in "Shape" indicates that a person is detected.

For example, the first line in FIG. 12 indicates that when the optical sensor 51 does not detect an object, but when the infrared camera 200 detects a heat source area determined as the type of object with which interference should be avoided, and when the shape of the heat source area is identified as a person, control is performed to reduce the driving speed of the holding arm 5.

This is because the shape of the heat source area determined as the type of object with which interference should be avoided is identified as a person, there is a high possibility that a person is present around the holding arm 5. However, because the optical sensor 51 does not detect an object, it is considered that the person is present at a location slightly away from the holding arm 5, and there is little need to immediately stop the holding arm 5.

Moreover, for example, the second line in FIG. 12 indicates that when the optical sensor 51 detects an object, when the infrared camera 200 detects a heat source area determined as the type of object with which interference should be avoided, and when the shape of the heat source area is identified as a person, the operation of the holding arm 5 is stopped. This is because there is a high possibility that the person is present at a location near the holding arm 5.

Moreover, for example, the third line in FIG. 12 indicates that when the optical sensor 51 does not detect an object, but when the infrared camera 200 detects a heat source area determined as the type of object with which interference should be avoided, and when the shape of the heat source area is identified as small in size, control is performed to display an alert. This is because although there is a small possibility that the heat source area is a person from the shape thereof, the shape may not be correctly identified.

Moreover, for example, the fourth line in FIG. 12 indicates that when the optical sensor 51 does not detect an object, but when the infrared camera 200 detects a heat source area determined as the type of object with which interference should be avoided, and when the shape of the heat source area is identified as elongated, control is performed to reduce the driving speed of the holding arm 5. This is because the shape of the heat source area determined as the type of object with which interference should be avoided is identified as elongated, it is considered that a tube is placed around the holding arm 5 and the tube needs to be prevented from being caught by the operation of the holding arm 5.

Furthermore, for example, the fifth line in FIG. 12 indicates that when the optical sensor 51 detects an object, when the infrared camera 200 detects a heat source area determined as the type of object with which interference should be avoided, and when the shape of the heat source area is identified as elongated, control is performed to reduce the driving speed of the holding arm 5. This is because the optical sensor 51 detects an object, and the shape of the heat source area determined as the type of object with which interference should be avoided is identified as elongated, it is considered that the tube is placed near the holding arm 5, and the tube needs to be prevented from being caught by the operation of the holding arm 5.

Because the top priority is to identify a person, the image analysis function 116 may also perform a process of identifying a person in the infrared image using a learned model generated by a learning process such as machine learning, deep learning, or the like, as a part of the recognition process of the shape of the heat source area determined as the type of object with which interference should be avoided. The learned model in this case, for example, is a learned model in which infrared image data is set as input side teacher data, and a detection pattern indicating the physique and posture of a person, temperature distribution, and the like are set as output side teacher data (correct answer data), and that has learned the relation between the input side teacher data and the output side teacher data.

Figure 13:
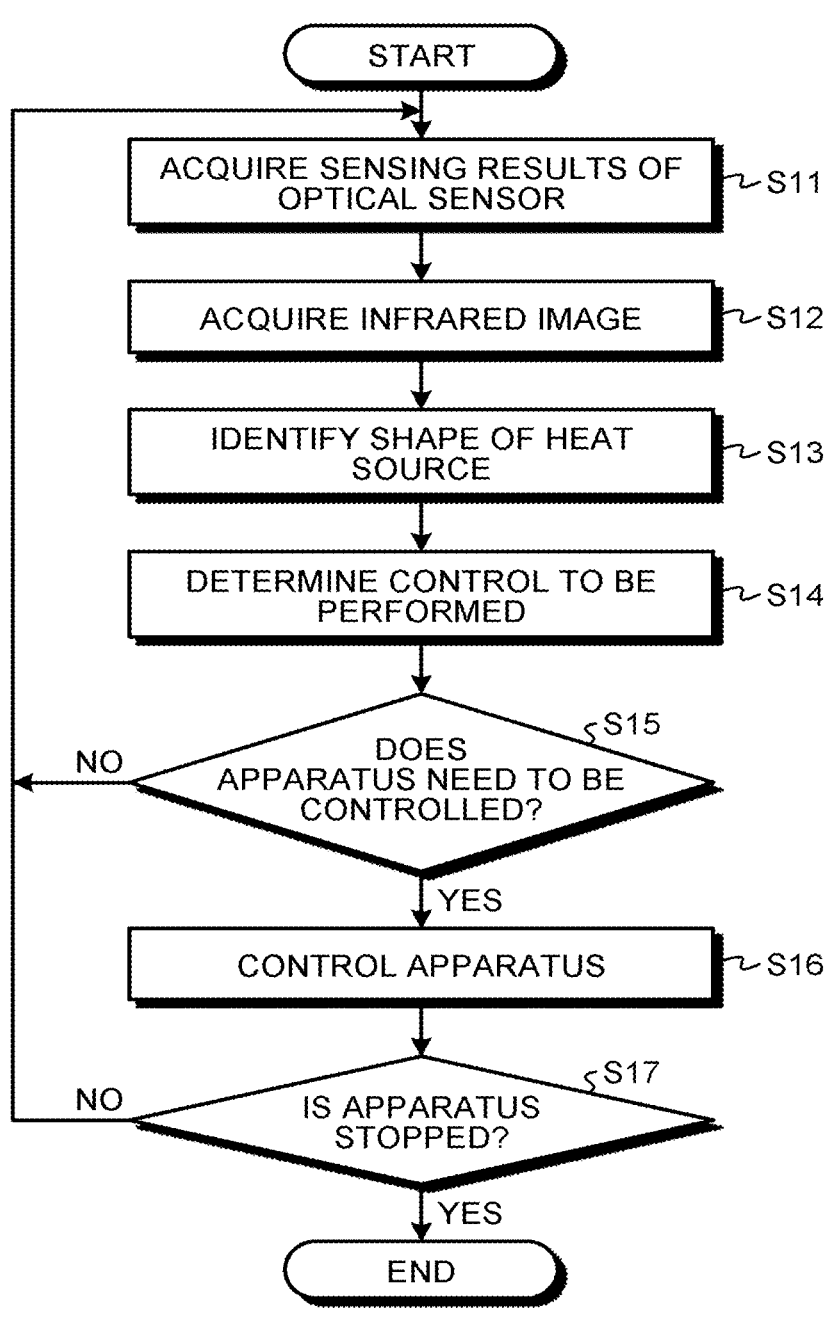
FIG. 13 is a flowchart illustrating an example of a process performed by the X-ray diagnostic apparatus according to the second embodiment.

Next, a process performed by the X-ray diagnostic apparatus 100*a* according to the present embodiment will be described. FIG. 13 is a flowchart illustrating an example of a process performed by the X-ray diagnostic apparatus 100*a* according to the second embodiment. Because steps S11 and S12 are the same as steps S1 and S2 in FIG. 8, the description thereof will be omitted.

After acquiring the infrared image at step S12, the image analysis function 116 performs a process of identifying the shape of the heat source area determined as the type of object with which interference should be avoided in the infrared image (step S13).

Next, on the basis of the sensing results of the optical sensor 51 obtained at step S11, the infrared image obtained at step S12, and the shape of the heat source area identified at step S13, the decision function 113a determines the control to be performed (step S14).

Because the processes subsequent to step S15 are the same as the processes subsequent to step S4 in FIG. 8, the description thereof will be omitted.

As described above, on the basis of the detection of an object by the optical sensor 51, the detection of a heat source area determined as the type of object with which interference should be avoided using an infrared image, and the shape of the identified heat source area, the X-ray diagnostic system Sa according to the second embodiment determines the control to be performed.

The X-ray diagnostic system Sa according to the second embodiment identifies the shape of a heat source area. Hence, it is possible to distinguish between a tube containing blood product or the like warmed up to about body temperature and a person. Consequently, for example, even if the optical sensor 51 is reacted to the tube, it is possible to estimate that the object is a tube. Hence, it is possible to prevent the operation of the holding arm 5 or the like from being stopped immediately.

Third Embodiment

In the second embodiment described above, a form in which the image analysis function 116 uses an infrared image to identify the shape of a heat source area has been described. In a third embodiment, a form of further specifying the location of a heat source area from a plurality of the infrared images will be described.

Figure 14:
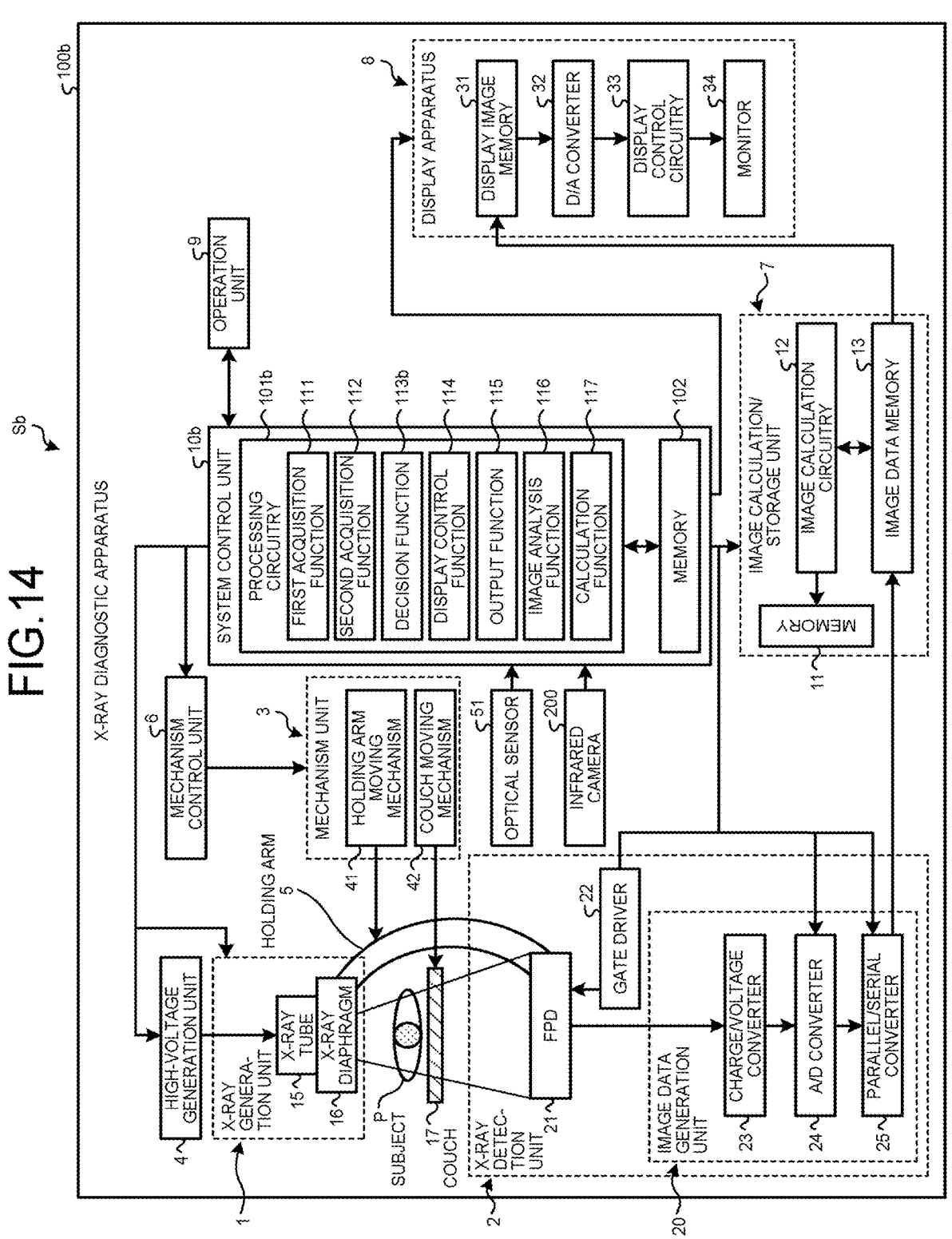
FIG. 14 is a block diagram illustrating an example of a configuration of an X-ray diagnostic apparatus according to a third embodiment.

Hereinafter, a configuration of a system control unit 10b of an X-ray diagnostic apparatus 100b of an X-ray diagnostic system Sb according to the third embodiment will be described. FIG. 14 is a block diagram illustrating an example of a configuration of the X-ray diagnostic apparatus 100b according to the third embodiment.

Processing circuitry 101b of the system control unit 10b of the third embodiment of the X-ray diagnostic apparatus 100b according to the third embodiment includes the first acquisition function 111, the second acquisition function 112, a decision function 113b, the display control function 114, the output function 115, the image analysis function 116, and a calculation function 117. Because the first acquisition function 111, the second acquisition function 112, the display control function 114, the output function 115, and the image analysis function 116 are the same as those in the first embodiment or the second embodiment, the description thereof will be omitted.

First, the calculation function 117 will be described. On the basis of a plurality of infrared images, the calculation function 117 specifies the location of a heat source area, by calculating the location of the heat source area determined as the type of object with which interference should be avoided. The calculation function 117 is an example of a calculation unit.

For example, on the basis of coordinates of a reference position in a portion configuring the X-ray diagnostic apparatus 100b (for example, an intersection between the floor rotary shaft of the holding arm 5 and the main rotary shaft of the holding arm, or the like), the reference position being the position that does not move even if the apparatus is operated, the calculation function 117 specifies the location of the heat source area by calculating the coordinates indicating the location of a heat source area determined as the type of object with which interference should be avoided in the infrared image. For example, the coordinates indicating the location of the heat source area are the coordinates of the center of gravity of the shape of the heat source area.

In the present embodiment, it is assumed that the infrared cameras 200 are installed such that a part of the field of view of each of the infrared cameras 200 overlaps with that of the other infrared camera. Moreover, at least one of the infrared cameras 200 includes the reference position of the X-ray diagnostic apparatus 100b within the field of view.

In this case, in the infrared image including the reference position, the calculation function 117 specifies the location of the heat source area, by calculating the coordinates indicating the location of the heat source area, on the basis of the relative positional relation of the coordinates of the reference position identified by the system control unit 10b, the reference position in the infrared image, the corresponding relation between the distance in the real space and the distance in the infrared image, and the location of the heat source area determined as the type of object with which interference should be avoided.

Even if the infrared image does not include the reference position, the infrared cameras 200 of the present embodiment are provided such that a part of the field of view of each of the infrared cameras overlaps with that of the other infrared camera. Hence, the calculation function 117 can specify the location of the heat source area by calculating the coordinates indicating the location of the heat source area determined as the type of object with which interference should be avoided in each of the infrared images, by obtaining the coordinates of the location overlapping with the infrared image including the reference position.

The decision function 113a determines the control to be performed, on the basis of the detection of an object by the optical sensor 51, the detection of a heat source area determined as the type of object with which interference should be avoided using an infrared image, the shape of the object in the infrared image, and the relative positional relation between the target position to be controlled and the location of the heat source area. For example, the target position is the tube of the X-ray tube 15 of the holding arm 5, the couchtop of the couch 17, and the like.

Figure 15:
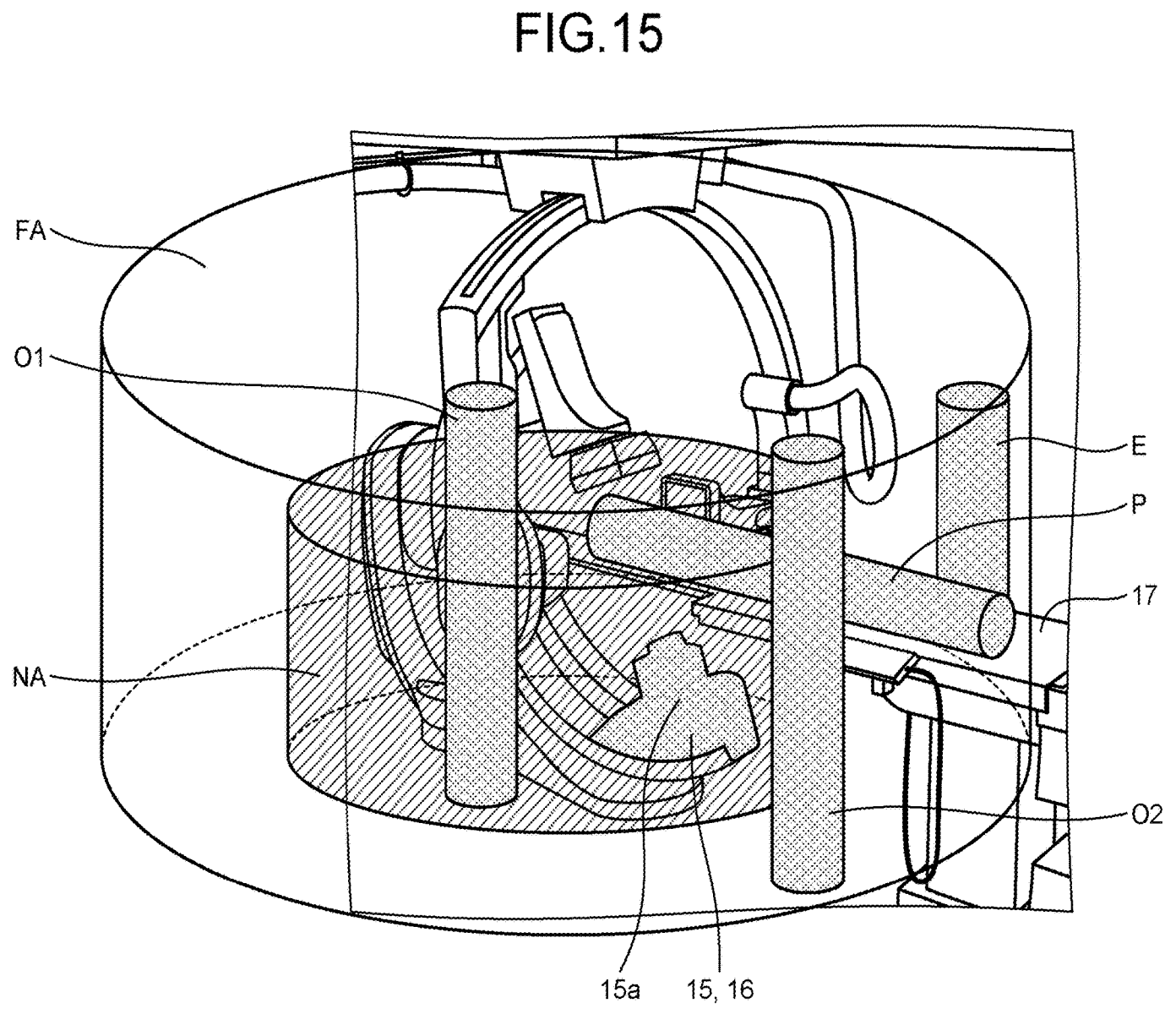

In this example, FIG. 15 is a diagram for explaining an example of a positional relation between the C-arm 5a and a person present in the examination room. In FIG. 15, an operator O1 (user), an operator O2, a radiologic technologist E, and the subject P are present in the examination room. Moreover, in FIG. 15, the target position is a tube 15a of the X-ray tube 15. Furthermore, in FIG. 15, a near area NA indicates an area near the target position, and a far area FA indicates an area far from the target position. An area near the target position is an example of a predetermined range of the movable unit.

For example, on the basis of the coordinates of the current location of the tube 15a of the X-ray tube 15 and the coordinates of the location of the heat source area calculated by the calculation function 117, the decision function 113b determines that the operator O1 is present in the near area NA, and the operator O2 and the radiologic technologist E are present in the far area FA.

In FIG. 15, the positional relation between the heat source area determined as the type of object with which interference should be avoided and the target position is determined in two stages of "Far" and "Near". However, the decision function 113b may also determine the positional relation between the heat source area determined as the type of object with which interference should be avoided and the target position in three stages or more.

For example, the decision function 113b may determine the positional relation between the heat source area determined as the type of object with which interference should be avoided and the target position in five stages of "In vicinity of optical sensor (the relative positional relation is closer than "Near")", "Near", "Within rotational range of C-arm 5a (the relative positional relation is between "Near" and "Far")", "Far", and "Out of detection range (the relative positional relation is further away than "Far")".

In this example, FIG. 16 is a diagram illustrating an example of a decision table 102c according to the third embodiment. "Position" in the decision table 102c indicates the relative positional relation between the location of the heat source area determined as the type of object with which interference should be avoided that is calculated by the calculation function 117, and the target position of the X-ray diagnostic apparatus 100. Moreover, "Detection" in "Shape" indicates that a person is detected.

For example, the first line in FIG. 16 indicates that when the optical sensor 51 detects an object, when the infrared camera 200 detects a heat source area determined as the type of object with which interference should be avoided, when the shape of the heat source area is identified as a person, and when the relative positional relation between the heat source area and the target position is in the vicinity of the optical sensor, control is performed to stop driving the holding arm 5.

This is because the optical sensor 51 also detects an object, the shape of the heat source area determined as the type of object with which interference should be avoided is identified as a person, and the relative positional relation is determined to be near, it is considered that a person is present very close to the holding arm 5, and there is a high possibility that the holding arm 5 comes into contact with the person.

Moreover, for example, the second line in FIG. 16 indicates that when the optical sensor 51 does not detect an object, but when the infrared camera 200 detects a heat source area determined as the type of object with which interference should be avoided, when the shape of the heat source area is identified as a person, and when the relative positional relation between the heat source area and the target position is near, control is performed to stop driving the holding arm 5.

This is because although the optical sensor 51 does not detect an object, the shape of the heat source area is identified as a person, and the relative positional relation is determined as near, there is a high possibility that a person is present near the holding arm 5, and it is considered preferable to prevent the holding arm 5 from coming into contact with the person in an early stage.

Furthermore, for example, the third line in FIG. 16 indicates that when the optical sensor 51 does not detect an object, but when the infrared camera 200 detects a heat source area determined as the type of object with which interference should be avoided, when the shape of the heat source area is identified as a person, and when the relative positional relation between the heat source area and the target position is within the rotational range of the holding arm 5, control is performed to reduce the driving speed of the holding arm 5.

This is because although it is considered that a person is not present near the holding arm 5, there is a high possibility that a person is present within the rotational range of the holding arm 5, and when the holding arm 5 is moved quickly, the holding arm 5 may come into contact with the person.

Still furthermore, for example, the fourth line in FIG. 16 indicates that when the optical sensor 51 does not detect an object, but when the infrared camera 200 detects a heat source area determined as the type of object with which interference should be avoided, when the shape of the heat source area is identified as a person, and when the relative positional relation between the heat source area and the target position is far, control is performed to notify the user with an alert.

This is because although a heat source area determined as the type of object with which interference should be avoided is detected, the relative positional relation between the heat source area and the target position is far, it is possible to determine that the effect is small. In this case, if the user is notified with an alert, it is considered that the user will move the holding arm 5 with caution.

Still furthermore, for example, the fifth line in FIG. 16 indicates that when the optical sensor 51 does not detect an object, but when the infrared camera 200 detects a heat source area determined as the type of object with which interference should be avoided, when the size of the heat source area is identified to be small, and when the relative positional relation between the heat source area and the target position is in the vicinity of the optical sensor 51, control is performed to notify the user with an alert and to reduce the driving speed of the holding arm 5.

This is because the size of the heat source area determined as the type of object with which interference should be avoided is small, there is a small possibility that a person is present. However, the detection may be erroneous and because the heat source area determined as the type of object with which interference should be avoided is present very close to the holding arm 5, it is preferable to warn the user to be careful.

Still furthermore, for example, the sixth line in FIG. 16 indicates that when the optical sensor 51 detects an object, when the infrared camera 200 detects a heat source area determined as the type of object with which interference should be avoided, when the size of the heat source area is identified as elongated, and when the relative positional relation between the heat source area and the target position is in the vicinity of the optical sensor 51, control is performed to reduce the driving speed of the holding arm 5.

This is because there is a high possibility that the laser light L emitted from the optical sensor 51 is blocked by the tube, there is no need to stop the holding arm 5 as long as the tube is prevented from being caught when the holding arm 5 is moved.

Still furthermore, for example, the seventh line in FIG. 16 indicates that when the optical sensor 51 detects an object, but when the infrared camera 200 does not detect a heat source area determined as the type of object with which interference should be avoided, control is performed to notify the user with an alert.

This is because although the optical sensor 51 detects an object, a heat source area determined as the type of object with which interference should be avoided is not detected around the holding arm 5, there is a high possibility that the laser light L emitted from the optical sensor 51 is blocked by a drape or the like.

For example, if the holding arm 5 is stopped in this case, it takes time to recover, and the user's operability is significantly degraded. In this case, in the present embodiment, by only notifying the user with an alert to check the surroundings, it is possible to prevent the procedure from being interrupted by an object other than a person.

As described above, the decision function 113*b* performs the process of determining the control to be performed, on the basis of the detection of an object by the optical sensor 51, the detection of a heat source area using an infrared image, the shape of the object in the infrared image, and the relative positional relation between the target position to be controlled and the location of the heat source area. However, the decision function 113*b* may also determine the control to be performed, on the basis of the detection of an object by the optical sensor 51, the detection of a heat source area using an infrared image, and the relative positional relation between the target position to be controlled and the location of the heat source area.

Figure 17:
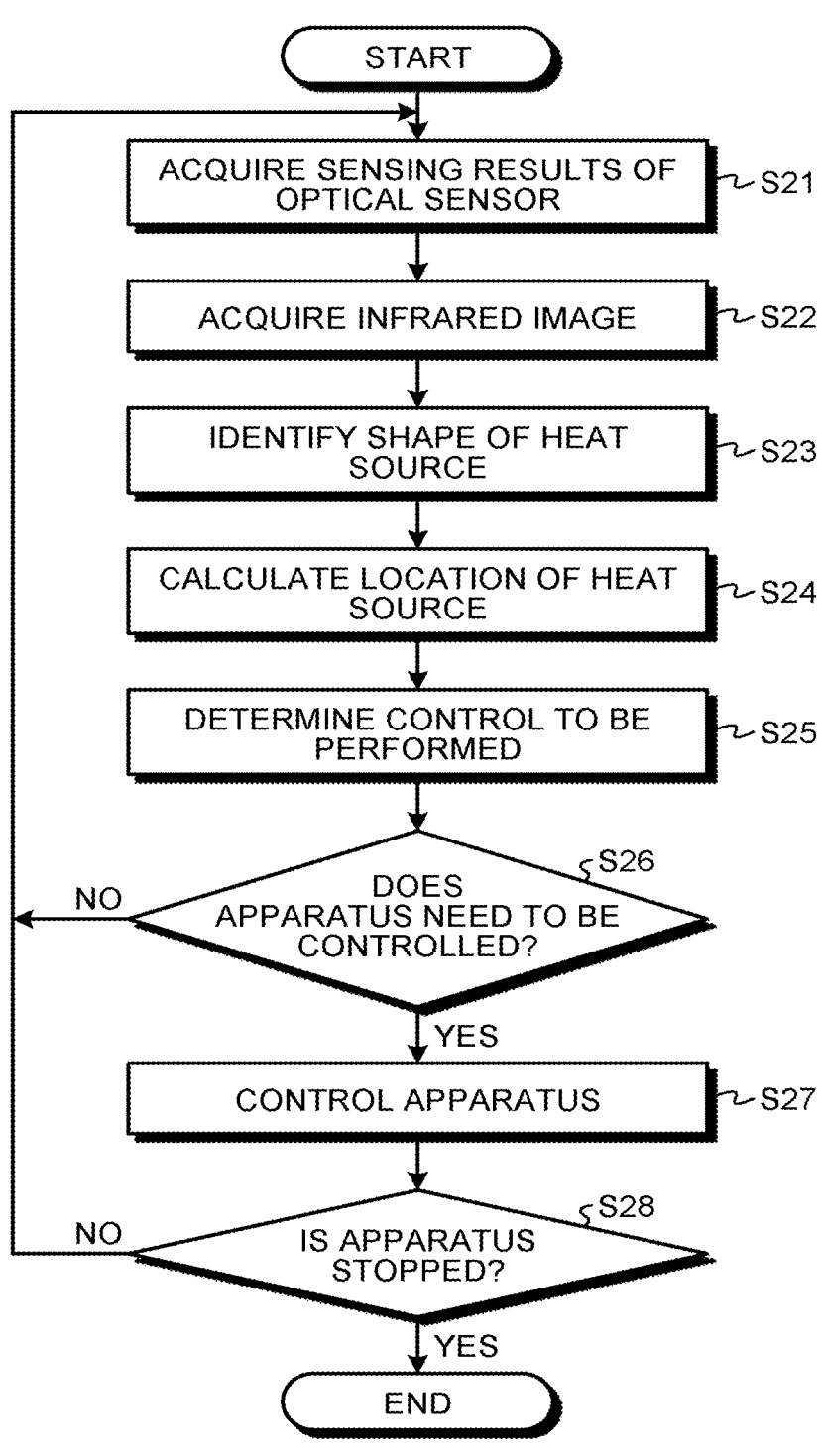
FIG. 17 is a flowchart illustrating an example of a process performed by the X-ray diagnostic apparatus according to the third embodiment.

Next, a process performed by the X-ray diagnostic apparatus 100*b* according to the present embodiment will be described. FIG. 17 is a flowchart illustrating an example of a process performed by the X-ray diagnostic apparatus 100*b* according to the third embodiment. Because steps S21 to S23 are the same as steps S11 to S13 in FIG. 13, the description thereof will be omitted.

After performing the recognition process of the shape of the heat source area at step S23, the calculation function 117 performs a process of calculating the location of the heat source area determined as the type of object with which interference should be avoided in the infrared image (step S24). For example, the calculation function 117 calculates the coordinates indicating the location of the heat source area, on the basis of the relative positional relation of the coordinates of the reference position of the X-ray diagnostic apparatus 100*b*, the reference position in the infrared image, and the location of the heat source area determined as the type of object with which interference should be avoided.

Next, on the basis of the sensing results of the optical sensor 51 obtained at step S21, the infrared image obtained at step S22, the shape of the heat source area identified at step S23, and the relative positional relation between the target position determined from the location of the heat source area determined as the type of object with which interference should be avoided that is calculated at step S24 and the heat source area, the decision function 113*a* determines the control to be performed (step S25).

Because the processes subsequent to step S26 are the same as the processes subsequent to step S15 in FIG. 13, the description thereof will be omitted.

As described above, on the basis of the detection of an object by the optical sensor 51, the detection of a heat source area determined as the type of object with which interference should be avoided using an infrared image, the shape of the identified heat source area, and the relative positional relation between the target position to be controlled and the location of the heat source area, the X-ray diagnostic system Sb according to the third embodiment determines the control to be performed.

The X-ray diagnostic system Sb according to the third embodiment performs control according to the relative positional relation between the target position to be controlled and the location of the heat source area determined as the type of object with which interference should be avoided. Hence, for example even if a person is detected, when the relative positional relation between the location of the tube of the X-ray tube 15 and the location of the heat source area determined as the type of object with which interference should be avoided is far, it is possible to determine that the effect is small and continue the operation of the holding arm 5. That is, with the X-ray diagnostic system Sb according to the third embodiment, it is possible to improve the operability of the X-ray diagnostic apparatus 100*b* by the user.

The embodiments described above can also be appropriately modified and implemented by changing a part of the configuration or function of each of the apparatuses. Therefore, in the following, a modification according to the embodiment described above will be described as another embodiment. In the following, points different from the embodiment described above will be mainly described, and detailed description of points common to the contents already described above will be omitted. Moreover, the modifications described below may be implemented individually or in combination as appropriate.

Modification

The above embodiment describes a form in which the decision function 113 determines the classification of an object on the basis of an infrared image captured by the infrared camera 200 capable of capturing images of the X-ray diagnostic apparatus 100. However, the decision function 113 may also determine the classification of an object on the basis of a visible light image captured by a camera capable of capturing images of the X-ray diagnostic apparatus 100.

For example, in the present modification, the decision function 113 identifies the form of an object in the visible light image, and determines the classification of the object. As an example, the decision function 113 determines the classification of the object itself, from the shape of the heat source area within a predetermined temperature range. Then, the decision function 113 determines whether the determined classification of the object is the type of object with which interference should be avoided, on the basis of determination information in which whether interference should be avoided is defined for each classification of object.

Moreover, for example, the decision function 113 may also determine the control contents to be performed by the X-ray diagnostic apparatus 100 on the basis of a visible light image, or may determine the control contents to be performed by the X-ray diagnostic apparatus 100 on the basis of a visible light image and an infrared image.

For example, when the control contents are determined on the basis of the visible light image, the decision function 113 determines the control contents, on the basis of the determined classification of the object and the relative positional relation between the target position to be controlled and the location of the object.

Furthermore, for example, when the control contents are determined on the basis of the visible light image and the infrared image, the decision function 113 specifies the location of the heat source area determined as the type of object with which interference should be avoided in the infrared image, on the visible light image of the heat source area. Next, the decision function 113 performs a process of identifying the shape of the object corresponding to the heat source area specified on the visible light image.

Then, similar to the third embodiment, on the basis of the detection of an object by the optical sensor 51, the detection of a heat source area determined as the type of object with which interference should be avoided using an infrared image, the shape of the object corresponding to the heat source area identified on the visible light image, and the relative positional relation between the target position to be controlled and the location of the object, the decision function 113 determines the control to be performed.

According to the present modification, it is possible to determine the classification of the object more accurately, because the classification of the object can be determined using a visible light image.

According to at least one of the embodiments described above, it is possible to improve the operability of the X-ray diagnostic apparatus by the user.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
processing circuitry configured to
   acquire a sensing result of a sensor, the sensor being provided in a movable unit configured to move freely in an examination room where X-ray imaging of a subject is performed, to detect a presence or an absence of an object around the movable unit,
   acquire an infrared image from an infrared camera provided in the examination room, the infrared image being an image in which an infrared ray emitted from an object present in a movable range is visualized,
   control an operation to be performed by the X-ray diagnostic apparatus in accordance with a combination of the acquired sensing result and a temperature of the object present in the movable range, the temperature being derived from the acquired infrared image.

2. The X-ray diagnostic apparatus according to claim 1, wherein the processing circuitry is further configured to:
   determine whether a classification of the object is an object to be avoided with which contact with the movable unit ought to be avoided, and
   when the classification of the object is determined as the object to be avoided, perform a control to prevent the movable unit from coming into contact with the object to be avoided.

3. The X-ray diagnostic apparatus according to claim 2, wherein the processing circuitry is further configured to determine the classification of the object present in the movable range, based on the acquired infrared image.

4. The X-ray diagnostic apparatus according to claim 3, wherein the processing circuitry is further configured to determine whether the object to be avoided is present in the movable range, based on a temperature of a heat source area belonging to a predetermined temperature range indicated in the infrared image.

5. The X-ray diagnostic apparatus according to claim 4, wherein the processing circuitry is further configured to:
   when the object to be avoided is determined to be present in the movable range, detect a positional relation between the movable unit and the object to be avoided in the movable range, based on the infrared image, and
   control the operation according to the X-ray imaging, based on a detection result.

6. The X-ray diagnostic apparatus according to claim 5, wherein the processing circuitry is further configured to determine the heat source area in the temperature range, which is set based on an average body temperature of a human as the object to be avoided, in the infrared image.

7. The X-ray diagnostic apparatus according to claim 5, wherein the processing circuitry is further configured to:

determine the classification of the object to be avoided present in the movable range, based on a shape of the heat source area in the predetermined temperature range indicated in the infrared image, and
   control the operation according to the X-ray imaging, based on the classification of the object to be avoided.

8. The X-ray diagnostic apparatus according to claim 7, wherein when the classification of the object to be avoided is other than a person, the processing circuitry is further configured to maintain or change a driving speed of the movable unit.

9. The X-ray diagnostic apparatus according to claim 8, wherein when the classification of the object to be avoided is other than a person, the processing circuitry is further configured to reduce the driving speed of the movable unit.

10. The X-ray diagnostic apparatus according to claim 8, wherein when the classification of the object to be avoided is a person, the processing circuitry is further configured to stop driving the movable unit.

11. The X-ray diagnostic apparatus according to claim 5, wherein the processing circuitry is further configured to,
   based on a location of the heat source area in the predetermined temperature range indicated in the infrared image and a location of a movable unit in the movable range corresponding to the infrared image, detect whether the heat source area is present within a predetermined range of the movable unit, and
   when the classification of the object is determined as the object to be avoided, reduce a driving speed of the movable unit or stop driving the movable unit, according to a detection result of whether the heat source area is present within the predetermined range.

12. The X-ray diagnostic apparatus according to claim 11, wherein when the heat source area is not present within the predetermined range, the processing circuitry is further configured to reduce the driving speed of the movable unit.

13. The X-ray diagnostic apparatus according to claim 5, wherein the processing circuitry is further configured to:
   based on a location of the heat source area in the predetermined temperature range indicated in the infrared image and a location of a movable unit in the movable range corresponding to the infrared image, detect whether the heat source area is present within a predetermined range of the movable unit, and
   when the classification of the object is determined as the object to be avoided, and when the heat source area is determined to be present within the predetermined range, stop driving the movable unit.

14. The X-ray diagnostic apparatus according to claim 4, wherein the processing circuitry is further configured to:
   control the movable unit to stop operating, when both the object and the heat source area are detected,
   issue an alert to notify a user of a possibility that a person is present around the movable unit, when the object is detected and the heat source area is not detected, and
   control the movable unit to reduce a driving speed of the movable unit, when the object is not detected and the heat source area is detected.

15. The X-ray diagnostic apparatus according to claim 3, wherein the movable unit includes an imaging unit configured to perform the X-ray imaging of the subject and a couch where the subject is placed.

16. The X-ray diagnostic apparatus according to claim 15, wherein the processing circuitry is further configured to acquire the infrared image in which an image of an area in a vicinity of a pedestal that supports the imaging unit is captured.

17. The X-ray diagnostic apparatus according to claim 15, wherein the processing circuitry is further configured to acquire the infrared image in which an image of a support that supports the couch is captured.

18. A control method for an X-ray diagnostic apparatus, comprising:

acquiring a sensing result of a sensor, the sensor being provided in a movable unit configured to move freely in an examination room where X-ray imaging of a subject is performed, to detect presence or absence of an object around the movable unit;

acquiring an infrared image from an infrared camera provided in the examination room, the infrared image being an image in which an infrared ray emitted from an object present in a movable range is visualized; and controlling an operation to be performed by the X-ray diagnostic apparatus in accordance with a combination of the acquired sensing result and a temperature of the object present in the movable range, the temperature being derived from the acquired infrared image.

19. The control method for the X-ray diagnostic apparatus according to claim 18, further comprising:

determining whether a classification of the object is an object to be avoided with which contact with the movable unit ought to be avoided, and wherein when the classification of the object is determined as the object to be avoided, performing a control to prevent the movable unit from coming into contact with the object to be avoided.

20. An X-ray diagnostic system, comprising:

at least one sensor;

at least one infrared camera; and an X-ray diagnostic apparatus, wherein the at least one sensor is provided in a movable unit configured to move freely in an examination room where X-ray imaging of a subject is performed, to detect a presence or an absence of an object around the movable unit, the at least one infrared camera is provided in the examination room, to capture an infrared image in which an infrared ray emitted from an object present in a movable range is visualized, and the X-ray diagnostic apparatus includes processing circuitry configured to acquire a sensing result from the at least one sensor, and control an operation to be performed by the X-ray diagnostic apparatus in accordance with a combination of the acquired sensing result and a temperature of the object present in the movable range the temperature being derived from the captured infrared image.

* * * * *